US011589773B2

(12) United States Patent
Zaman et al.

(10) Patent No.: US 11,589,773 B2
(45) Date of Patent: *Feb. 28, 2023

(54) MEMS DEVICE FOR AN IMPLANT ASSEMBLY

(71) Applicant: ENDOTRONIX, INC., Lisle, IL (US)

(72) Inventors: Mohammad Faisal Zaman, Naperville, IL (US); Jeffrey Fong, Chicago, IL (US); Julian Chee, De Pere, WI (US); Tyler Panian, Naperville, IL (US); Michael Nagy, Lombard, IL (US)

(73) Assignee: ENDOTRONIX, INC., Lisle, IL (US)

( * ) Notice: Subject to any disclaimer, the term of this patent is extended or adjusted under 35 U.S.C. 154(b) by 800 days.

This patent is subject to a terminal disclaimer.

(21) Appl. No.: 16/251,146

(22) Filed: Jan. 18, 2019

(65) Prior Publication Data

US 2019/0150785 A1 May 23, 2019

Related U.S. Application Data

(63) Continuation-in-part of application No. 15/837,075, filed on Dec. 11, 2017, now Pat. No. 10,433,764, and
(Continued)

(51) Int. Cl.
*A61B 5/07* (2006.01)
*A61B 5/00* (2006.01)
(Continued)

(52) U.S. Cl.
CPC ............ *A61B 5/076* (2013.01); *A61B 5/0031* (2013.01); *A61B 5/01* (2013.01); *A61B 5/0215* (2013.01);
(Continued)

(58) Field of Classification Search
None
See application file for complete search history.

(56) References Cited

U.S. PATENT DOCUMENTS 4,026,276 A 5/1977 Chubbuck
5,257,542 A * 11/1993 Voss ...................... G01L 9/125
361/283.4
(Continued)

FOREIGN PATENT DOCUMENTS

CA 2840645 A1 1/2013
CN 1701464 A 11/2005
(Continued)

OTHER PUBLICATIONS

PCT International Search Report relating to PCT/US2019/014108, dated Apr. 9, 2019.
(Continued)

*Primary Examiner* — Michael R Bloch
(74) *Attorney, Agent, or Firm* — McDonald Hopkins LLC

(57) ABSTRACT

Disclosed is an implant and method of making an implant. The implant having a housing that defines a cavity. The housing includes a sensor comprising a base attached to a diaphragm wherein said base may be positioned within said cavity. The sensor may be a capacitive pressure sensor. The diaphragm may be connected to the housing to hermetically seal said housing. The sensor may include electrical contacts positioned on the diaphragm. The attachment between the base and the diaphragm may define a capacitive gap and at least one discontinuity configured to enhance at least one performance parameter of said implant.

26 Claims, 17 Drawing Sheets

Related U.S. Application Data a continuation-in-part of application No. 15/213,712, filed on Jul. 19, 2016, now Pat. No. 10,638,955, which is a continuation-in-part of application No. 14/777,654, filed as application No. PCT/US2014/030661 on Mar. 17, 2014, now Pat. No. 10,226,218, which is a continuation of application No. 14/129,725, filed as application No. PCT/US2012/044998 on Jun. 29, 2012, now Pat. No. 9,867,552.

(60) Provisional application No. 62/618,848, filed on Jan. 18, 2018, provisional application No. 61/786,793, filed on Mar. 15, 2013, provisional application No. 61/502,982, filed on Jun. 30, 2011.

(51) Int. Cl.
*A61B 5/01* (2006.01)
*A61B 5/0215* (2006.01)
*A61B 5/03* (2006.01)
*A61B 5/08* (2006.01)

(52) U.S. Cl.
CPC .......... *A61B 5/02152* (2013.01); *A61B 5/036* (2013.01); *A61B 5/6876* (2013.01); *A61B 5/08* (2013.01); *A61B 5/6869* (2013.01); *A61B 2562/0247* (2013.01); *A61B 2562/168* (2013.01)

(56) References Cited

U.S. PATENT DOCUMENTS

| | | | |
|---|---|---|---|
| 5,454,270 A | 10/1995 | Brown et al. | |
| 5,510,276 A | 4/1996 | Diem et al. | |
| 5,840,148 A | 11/1998 | Campbell et al. | |
| 6,939,299 B1 | 9/2005 | Petersen et al. | |
| 7,059,195 B1 | 6/2006 | Liu et al. | |
| 7,174,212 B1 | 2/2007 | Klehn et al. | |
| 7,191,013 B1 | 3/2007 | Miranda et al. | |
| 7,290,454 B2 | 11/2007 | Liu | |
| 7,353,711 B2 | 4/2008 | O'Dowd et al. | |
| 7,401,521 B2 | 7/2008 | Bellini et al. | |
| 7,432,723 B2 | 10/2008 | Ellis et al. | |
| 7,498,799 B2 | 3/2009 | Allen et al. | |
| 7,550,978 B2 | 6/2009 | Joy et al. | |
| 7,574,792 B2 | 8/2009 | O'Brien et al. | |
| 7,686,762 B1 | 3/2010 | Najafi et al. | |
| 7,763,487 B2 | 7/2010 | Villa et al. | |
| 7,932,732 B2 | 4/2011 | Ellis et al. | |
| 7,936,174 B2 | 5/2011 | Ellis et al. | |
| 7,973,540 B2 | 7/2011 | Kroh et al. | |
| 8,014,865 B2 | 9/2011 | Najafi et al. | |
| 8,104,358 B1 | 1/2012 | Jia et al. | |
| 8,111,150 B2 | 2/2012 | Miller et al. | |
| 8,118,748 B2 | 2/2012 | Schugt et al. | |
| 8,132,465 B1 | 3/2012 | Doelle et al. | |
| 8,154,389 B2 | 4/2012 | Rowland et al. | |
| 8,159,348 B2 | 4/2012 | Ellis | |
| 8,237,451 B2 | 8/2012 | Joy et al. | |
| 8,360,984 B2 | 1/2013 | Yadav et al. | |
| 8,373,559 B2 | 2/2013 | Mccain | |
| 8,424,388 B2 | 4/2013 | Mattes et al. | |
| 8,493,187 B2 | 7/2013 | Rowland et al. | |
| 8,512,252 B2 | 8/2013 | Ludomirsky et al. | |
| 8,565,866 B2 | 10/2013 | Blomqvist et al. | |
| 8,665,086 B2 | 3/2014 | Miller et al. | |
| 8,669,770 B2 | 3/2014 | Cros | |
| 8,700,924 B2 | 4/2014 | Mian et al. | |
| 8,870,787 B2 | 10/2014 | Yadav et al. | |
| 8,901,775 B2 | 12/2014 | Armstrong et al. | |
| 9,265,428 B2 | 2/2016 | O'Brien et al. | |
| 9,305,456 B2 | 4/2016 | Rowland et al. | |
| 9,496,924 B2 | 11/2016 | Aber et al. | |
| 9,498,130 B2 | 11/2016 | Najafi et al. | |
| 9,712,894 B2 | 7/2017 | Lee et al. | |
| 9,839,732 B2 | 12/2017 | Armstrong et al. | |
| 10,022,054 B2 | 7/2018 | Najafi et al. | |
| 10,105,103 B2 | 10/2018 | Goldshtein et al. | |
| 10,143,388 B2 | 12/2018 | Cros et al. | |
| 10,205,488 B2 | 2/2019 | Hershko et al. | |
| 10,307,067 B1 | 6/2019 | Xu | |
| 10,383,575 B2 | 8/2019 | Najafi et al. | |
| 10,478,067 B2 | 11/2019 | Najafi et al. | |
| 10,687,709 B2 | 6/2020 | Najafi et al. | |
| 10,687,716 B2 | 6/2020 | Goldshtein et al. | |
| 10,709,341 B2 | 7/2020 | White et al. | |
| 10,874,349 B2 | 12/2020 | Goldshtein et al. | |
| 10,874,479 B2 | 12/2020 | Forsell | |
| 11,154,207 B2 | 10/2021 | Campbell et al. | |
| 11,206,988 B2 | 12/2021 | Goldshtein et al. | |
| 2006/0109188 A1 | 5/2006 | Ikeda et al. | |
| 2006/0137461 A1 | 6/2006 | Bellini et al. | |
| 2006/0177956 A1 | 8/2006 | O'Brien et al. | |
| 2006/0241354 A1 | 10/2006 | Allen | |
| 2006/0287602 A1* | 12/2006 | O'Brien | A61B 5/0031 600/561 |
| 2007/0118038 A1* | 5/2007 | Bodecker | A61B 5/0215 128/903 |
| 2007/0163355 A1 | 7/2007 | Nassar et al. | |
| 2007/0199385 A1 | 8/2007 | O'Brien | |
| 2007/0208390 A1 | 9/2007 | Von Arx et al. | |
| 2007/0267708 A1* | 11/2007 | Courcimault | B81C 1/00301 257/414 |
| 2008/0269573 A1 | 10/2008 | Najafi et al. | |
| 2008/0269829 A1 | 10/2008 | Li et al. | |
| 2009/0221885 A1 | 9/2009 | Hall et al. | |
| 2011/0046452 A1 | 2/2011 | Najafi et al. | |
| 2011/0063088 A1 | 3/2011 | Stevenson et al. | |
| 2014/0028467 A1 | 1/2014 | Nagy et al. | |
| 2014/0155710 A1 | 6/2014 | Rowland et al. | |
| 2014/0306807 A1 | 10/2014 | Rowland et al. | |
| 2016/0029953 A1 | 2/2016 | Rowland | |
| 2016/0029956 A1 | 2/2016 | Rowland | |
| 2016/0324443 A1 | 11/2016 | Endotronix | |
| 2020/0022601 A1 | 1/2020 | Rogers et al. | |
| 2020/0297218 A1 | 9/2020 | White et al. | |
| 2021/0068681 A1 | 3/2021 | Campbell et al. | |
| 2021/0275733 A1 | 9/2021 | Goldshtein et al. | |

FOREIGN PATENT DOCUMENTS

| | | |
|---|---|---|
| CN | 1826686 A | 8/2006 |
| CN | 101128957 A | 2/2008 |
| CN | 101278439 A | 10/2008 |
| CN | 101427923 A | 5/2009 |
| JP | 2000005136 A | 1/2000 |
| JP | 2002515278 A | 5/2002 |
| JP | 2003144417 A | 5/2003 |
| JP | 2005284511 A | 10/2005 |
| JP | 2006309582 A | 11/2006 |
| JP | 2007256287 A | 10/2007 |
| JP | 2008022935 A | 2/2008 |
| JP | 2010538254 A | 12/2010 |
| WO | 2009146089 A1 | 12/2009 |
| WO | 2012015955 A1 | 2/2012 |
| WO | 2013033506 | 3/2013 |
| WO | 2014170771 A1 | 10/2014 |
| WO | 2017115112 | 7/2017 |

OTHER PUBLICATIONS

Patent Cooperation Treaty (PCT), International Search Report and Written Opinion for Application PCT/US12/44998, dated Sep. 25, 2012, 9 pgs., International Searching Authority, US.

Extended European Search Report for Application 12804636.4 PCT/US2012044998, dated Jan. 20, 2015, 6pgs., Eurpoean Patent Office, Germany.

Patent Cooperation Treaty (PCT), International Search Report and Written Opinion for Application PCT/US14/30661 dated Sep. 17, 2015, 8 pgs., International Searching Authority, US.

(56) References Cited

OTHER PUBLICATIONS

Extended European Search Report for Application 14806873.7 PCT/US2014030661, dated May 20, 2016, 7 pp., European Patent Office, Germany.
International Search Report and Written Opinion of the International Searching Authority for PCT/US2017/042702 dated Apr. 3, 2018, 17 pages.

* cited by examiner

MEMS DEVICE FOR AN IMPLANT ASSEMBLY

CROSS-REFERENCE TO RELATED APPLICATIONS

This application claims priority to and the benefit of each the following applications: U.S. Provisional Patent Application No. 62/618,848 entitled "MEMS DEVICE FOR AN IMPLANT ASSEMBLY," filed on Jan. 18, 2018. This application is also a continuation-in-part of U.S. patent application Ser. No. 15/213,712 entitled "PRESSURE SENSING IMPLANT" filed on Jul. 19, 2016 which is a continuation-in-part of U.S. patent application Ser. No. 14/777,654 entitled "PRESSURE SENSING IMPLANT" filed on Sep. 16, 2015 which is a national phase entry application that claims priority to International Patent Application No. PCT/US2014/030661 filed Mar. 17, 2014 which claims priority to Provisional Patent Application No. 61/786,793 entitled "PRESSURE SENSING IMPLANT," filed on Mar. 15, 2013. This application is also a continuation-in-part of U.S. patent application Ser. No. 15/837,075 entitled "IMPLANTABLE SENSOR ENCLOSURE WITH THIN SIDEWALLS," filed on Dec. 11, 2017, which claims priority to U.S. patent application Ser. No. 14/129,725 (U.S. Pat. No. 9,867,552) entitled "IMPLANTABLE SENSOR ENCLOSURE WITH THIN SIDEWALLS," filed on Feb. 21, 2014, which claims priority to International Patent Application No. PCT/US2012/044998 entitled "IMPLANTABLE SENSOR ENCLOSURE WITH THIN SIDEWALLS," filed on Jun. 29, 2012 which claims priority to Provisional Patent Application No. 61/502,982 entitled "IMPLANTABLE SENSOR ENCLOSURE WITH THIN SIDEWALLS," filed on Jun. 30, 2011, each of which are hereby incorporated by reference in its entireties.

FIELD OF INVENTION

This application relates to implanted sensor packages and more particularly to an improved structure for implanted sensor packages.

BACKGROUND

Implantable wireless sensors are useful in assisting diagnosis and treatment of many diseases. Examples of wireless sensor readers are disclosed in U.S. Pat. Nos. 8,154,389, and 8,493,187, each entitled Wireless Sensor Reader, which are incorporated by reference herein. In particular, there are many applications where measuring pressure from within a blood vessel deep in a patient's body is clinically beneficial. For example, measuring the pressure in the heart's pulmonary artery is helpful in optimizing treatment of heart failure and pulmonary hypertension. In this type of application, a sensor may need to be implanted up to 20 cm beneath the surface of the skin.

One type of implant for this application is described by U.S. patent application Ser. No. 15/213,712 ("the '712 application") which illustrates the use of floating bases and vented cavities within a hermetically sealed implant housing. Notably, these types of implants include micro-electromechanical systems (MEMS) having capacitive electrodes that transduce pressure to capacitance. The implants include a capacitive sensor that includes a flexible diaphragm and a less flexible (more rigid) base, with a cavity in between and capacitive electrodes at least partially extending within the cavity. The sensor may be fabricated having a diaphragm formed on one wafer and a base formed on a second wafer, in which the base is attached to the diaphragm around a perimeter. Two layers—diaphragm and base—thus form a capacitive sensor in which the base has a smaller overall area than the diaphragm. The sensor may then be attached to an implant housing by inserting the smaller-area base into a larger housing cavity of the implant housing and is hermetically sealed therein leaving an outer surface of the diaphragm exposed to the environment outside of the implant housing. The attachment line between the base and diaphragm within the implant housing may be referred to as a "bond line" and the cavity defined between the diaphragm and base may be identified as a "capacitive gap." The '712 application discusses various embodiments of these devices.

Known processes for bonding the two wafers together, forming the capacitive gap, generally cause various internal stresses at the bond line (i.e. point of bonding about the perimeter between the base and diaphragm). As such, a high-stress line may be formed around the perimeter of the cavity. The stress may relax over time slowly, and/or change with temperature. The stress may case the implant to sense or to generate inaccurate readings in capacitance over the life of the device as capacitance is changing in response to a parameter (e.g. stress or temperature) other than the desired measurement (e.g. pressure). Stress relaxation along the bond line may be a slow change over time which can cause signal drift due to slow change in capacitive gap height.

It has been identified that the physical features of the capacitive gap may be important to the functional performance of the pressure sensing implant. The capacitance, and hence the resonant frequency of the implant, depends on the change in distance between the capacitive electrodes. Thus, it is desirable to have an implant whose capacitance changes when the distance between the capacitive electrode (the gap height) changes, due to an external pressure. However, it is not desirable to also experience capacitance changes due to any other reason, including: slow changes in the composition of gas (or fluid) in the capacitive gap over time; slow changes in distance between plates due to relaxation of built-in internal stresses over time; and changes in temperature. These composition changes may cause error in implant readings because capacitance (and hence resonant frequency) may be changing for reasons other than due to external pressure. In one embodiment, the design of the implant is subject to a heightened level of sensitivity as a gap change of 1 percent (i.e. 10 nanometers) over time may be significant enough to put the implant out of its designed range or specified functionality.

Additionally, for implants with vented cavities as discussed above, there is a need for the composition of the gap fluid (i.e. liquid or gas) to stabilize quickly once the diaphragm and base wafer are hermetically sealed to the cavity of the implant housing. If, for example, a component within the implant housing (such as a PCB) outgasses water vapor into the housing cavity, and the vent between the housing cavity and capacitive gap is only a small hole, it may take a long time for the capacitive gap to achieve homogeneity with the outer housing cavity, causing long term inaccuracy while the stabilization (homogeneity) takes place.

Further challenges have been identified related to the practical implementation of such an implant. Particularly, it has been identified that an implant designed to meet the criteria above may also be sensitive to temperature and pressure changes, including while in ambient conditions, when positioned within a patient, and during transition between ambient conditions to in vivo. These temperature and pressure variations may cause the sensor to communicate inconsistent signals or otherwise function in an inconsistent manner. As such, in addition to providing an implant that includes desirable features including having high sensitivity, good electrical isolation between electrical nodes and surrounding body fluids or tissue, being highly stable over time, having good mechanical strength, incorporating biocompatible materials, minimizing the use of ferritic materials; the implant may also include a design that would increase mechanical strength and reduce the effects of changes to temperature and pressure stresses.

Thus, it is desirable to provide an improved implant to optimize desirable features and to ensure a consistent and reliable operation over the life of the implant. Further, because MEMS fabrication processes can be complex and require very long development times, it is desirable to identify designs that allow modifying performance specifications with only minor changes in structure. Such specifications for an implant include: sensitivity, full scale range, frequency offset, and avoidance of pull-in between capacitive electrodes. As such, there is a need for a capacitive MEMS pressure sensor with floating base and vented cavity that provides: reduced gap height error due to relaxation of internal stresses at the bond line; reduced gap height error due to changes in stress at the bond line, due to temperature changes; reduced capacitance error due to slow, long-term change of composition in the fluid (gas or liquid) in the gap; and to provide a cost-effective means to simply modify and control key design parameters such as sensitivity, full-scale range, maximum voltage withstand (pull-in resistance), and temperature sensitivity.

SUMMARY OF THE INVENTION

This application relates to hermetically packaged wireless electronics and more particularly to an implantable sensor design and manufacturing approach to optimize manufacturability, size, longevity, RF characteristics, and overall performance while minimizing potential effects of operating in various pressure conditions, temperature conditions and manufacturing induced stress conditions.

In an embodiment, an implant comprises a housing that defines a housing cavity that includes a sensor connected to said housing. Said sensor comprises a diaphragm configured to flex in response to external changes in pressure and a floating base attached to said diaphragm to define a capacitive gap between said diaphragm and said floating base. Said attachment is positioned along a perimeter of said capacitive gap wherein said floating base is positioned entirely within said cavity and wherein said attachment along said perimeter contains at least one discontinuity. The floating base may be attached only to said diaphragm. The sensor may be a capacitive pressure sensor. The diaphragm may be connected to said housing to form a hermetic seal about said housing cavity. The sensor may include at least one electrical contact positioned on said diaphragm. The at least one discontinuity may vent said capacitive gap to said housing cavity such that liquid or gas may pass between said gap and said housing cavity.

The at least one discontinuity may allow at least one electrical trace to connect at least one said electrical contact outside of said capacitive gap to at least one electrode positioned at least partially within said capacitive gap. The capacitive gap may include electrodes positioned on said diaphragm and said floating base. The implant may include a coil in electrical communication with said sensor, said coil positioned within said housing. The diaphragm may be made of a glass material and the floating base may be made of silicon. The diaphragm may include a thickness of about 195 μm and said at least one discontinuity may include a length of about 6.75 mm. The location and size of said at least one discontinuity may be configured to enhance at least one performance parameter of said implant. The at least one performance parameter may be selected from the following list: sensitivity to pressure, sensitivity to temperature, mechanical strength, and long term accuracy. Sensitivity to temperature may be improved by positioning said at least one discontinuity such that a coefficient of thermal expansion mismatch effect counteracts a gas expansion effect to reduce capacitive gap change due to temperature.

In another embodiment, provided is a method of assembling an implant The method comprises providing a housing that defines a cavity. A floating base may be attached to a diaphragm to form a capacitive gap, said attachment being positioned along a perimeter of said capacitive gap and including at least one discontinuity to enhance at least one performance parameter of said implant. The diaphragm may be attached to said housing such that said floating base is positioned within said cavity. A coil may be attached to said sensor. A bottom may be attached to said housing to form a hermetic seal about said cavity. The diaphragm may be hermetically attached to said housing by at least one laser weld about the perimeter of said cavity. The diaphragm may be made of a glass material and said floating base may be made of silicon.

In another embodiment, provided is an implant that comprises a housing that defines a cavity and having a sensor connected to said housing. The sensor comprising a diaphragm may have at least one diaphragm electrode. A base may be attached to said diaphragm, said base including at least one base electrode wherein said base and diaphragm define a capacitive gap between the at least one diaphragm electrode and the at least one base electrode. The base may attach to said diaphragm along a perimeter of said capacitive gap, said attachment including at least one discontinuity configured to enhance at least one performance parameter of said implant. The base may be positioned within the cavity of said housing. The base may further include at least one through hole to provide access to electrically connect said at least one electrode to a component outside said capacitive gap. The diaphragm may include a thickness between about 100 μm to about 300 μm. The implant may include a circuit having a resonant frequency that changes in response to a sensed parameter such as pressure. The implant may be filled with a liquid or gel or may be a vacuum or filed with a predetermined pressure. The base may include at least one through substrate via (TSV) to electrically connect the at least one of the base electrode and said diaphragm electrode to a component outside said capacitive gap. The diaphragm may include a thick region and a thin region wherein said thin region is aligned with said capacitive gap. The at least one performance parameter may be selected from the following list: sensitivity to pressure, sensitivity to temperature, mechanical strength, and long term accuracy. The sensitivity to temperature may be achieved by positioning said at least one discontinuity such that a coefficient of thermal expansion mismatch effect counteracts a gas expansion effect to reduce capacitive gap change due to temperature.

In yet another embodiment, provided is an implant that comprises a housing having a plurality of walls and at least one opening. A sensor may be connected to an opening in said housing, said sensor comprising a first layer having a first dimension and a second layer having a second dimension shorter than said first dimension. Said second layer may be positioned entirely within said housing and a surface of said first layer is exposed to the exterior of said housing. Said second layer may be attached to said first layer to define a capacitive gap between layers, said attachment being positioned along a perimeter of said capacitive gap. Said attachment along said perimeter may include at least one discontinuity. The location and position of said at least one discontinuity may be configured to enhance at least one performance parameter of said implant.

BRIEF DESCRIPTION OF THE DRAWINGS

Embodiments of the present disclosure are described herein with reference to the drawings wherein.

DETAILED DESCRIPTION OF THE PREFERRED EMBODIMENTS

Figure 1:
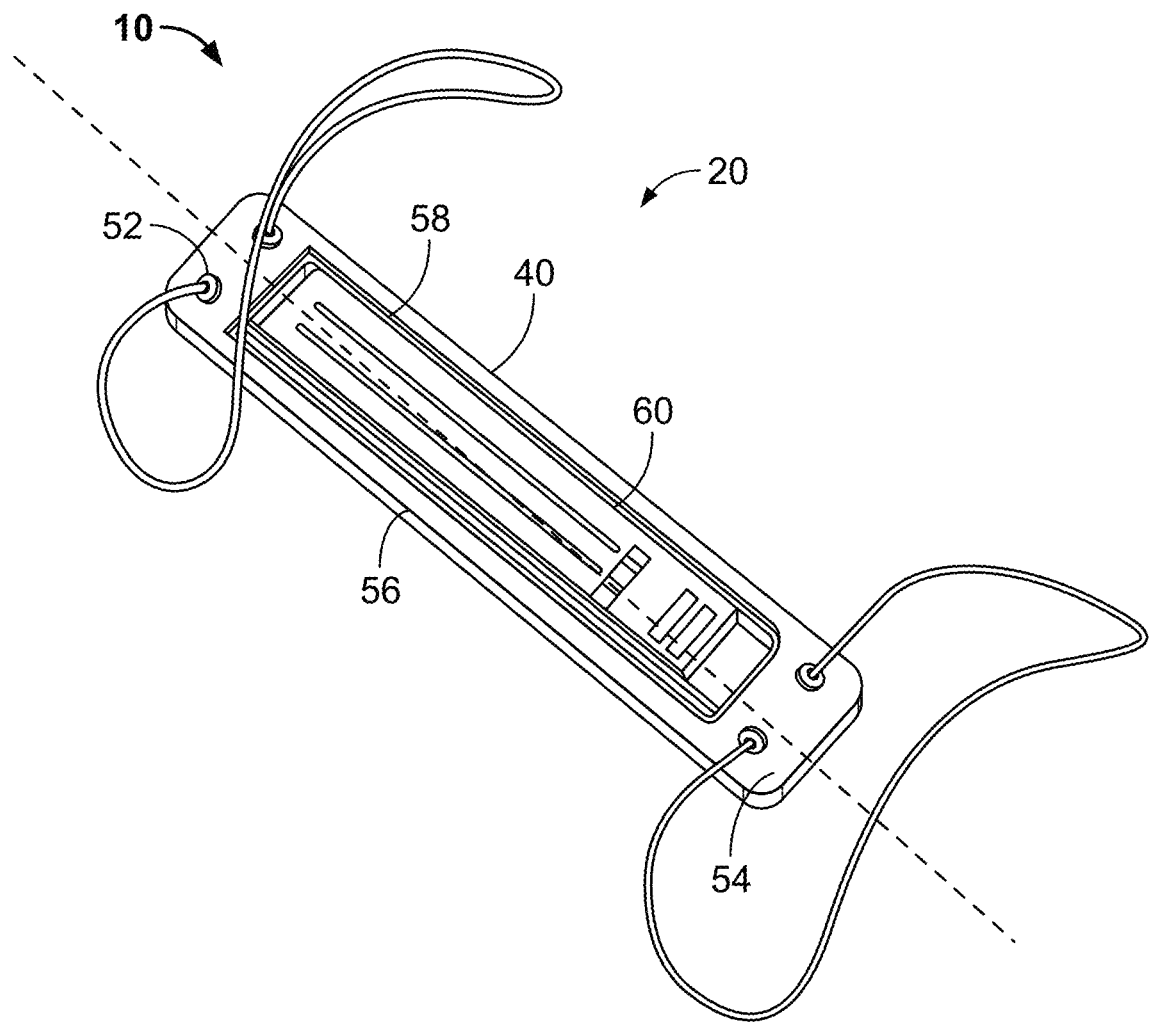
FIG. 1 is a perspective view of an embodiment for a wireless implant of the present disclosure.
Figure 2:
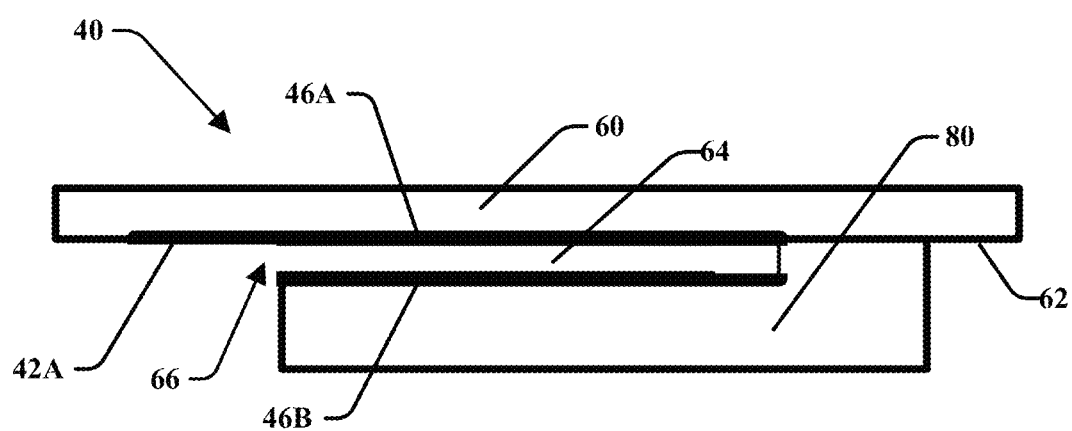
FIG. 2 is a schematic cross sectional view of a sensor component of the wireless implant of the present disclosure.

Reference will now be made in detail to embodiments of the invention, examples of which are illustrated in the accompanying drawings. It is to be understood that other embodiments may be utilized and structural and functional changes may be made without departing from the respective scope of the invention.

This application relates to an implant 10 and more particularly to an implantable sensor design and manufacturing approach to optimize manufacturability, size, longevity, RF characteristics, Q, and overall performance related to increasing sensitivity and minimizing thermally induced frequency offset. To improve the device design and to minimize thermally induced frequency offset, the implant may be constructed to optimize deflection of the surfaces of the implant capacitor while providing ample protection from the environment and maximizing space for the internal components such as the coil.

In one embodiment, the instant application refers to an improvement to the interaction of a bond line 74 and a capacitive gap 64 that exist between a diaphragm wafer 60 and a floating base wafer 80 described above and in application Ser. No. 15/213,712. The term "floating base" used in the instant application is illustrated in the '712 application and may refer to a wafer or layer that is attached or structurally supported by a wall (e.g. the diaphragm) of an implant housing and includes a smaller dimension than the wall. The floating base may appear to float within the housing cavity as it is structurally supported by just the diaphragm. In particular, it was identified that the performance of various pressure sensing implant designs may be manipulated by adjusting structural relationships between the continuity of the bond line 74 and the size of the capacitive gap 64 that exist between the diaphragm and base. The discovered relationship may assist with designing pressure sensing implants within various design constraints that improve the long term performance of the implant.

FIGS. 1 through 5B illustrate a wireless implant housing 20 that is described by the '712 application. Here, the sensor 40 may include the top wall or diaphragm 60 having electronic components placed thereon. The top wall 60 may remain a diaphragm once bonded together with the remaining side walls of the sensor housing 20. The sensor 40 may be a MEMS type sensor. The sensor 40 may be a capacitive type sensor, formed by attaching a base 80 to the diaphragm 60. In one embodiment, the capacitive gap 64 may be positioned between the base 80 and the diaphragm 60. At least one of the base 80 and the diaphragm 60 may be etched to create the capacitive gap 64 at least partially between the base 80 and the diaphragm 60. Electrodes 46A, 46B may be patterned on either side of the capacitive gap 64 (See FIGS. 2, and 4-6). Electrode 46A may be placed on the diaphragm 60 and electrode 46B may be placed on the base 80. Electrode 46A may terminate to bond pads 42A, 42B which may be available to connect the electrode 46A to other components in the implant 10. Note that the embodiments depicted in FIGS. 1-5B, there are two electrodes 46A, 46B positioned on base 80. Together, they form two capacitors in series. Other electrode combinations and configurations are possible, including those disclosed in the '712 application.

The capacitive gap 64 may be vented to the outside of the sensor 40 by vent 66. The vent 66 may be a break in the bond or weld line between base 80 and diaphragm 60, which allows electrical traces or interconnect of the electrodes 46A to pass through and connect bond pads 42A, 42B. The vent is identified in FIGS. 5A, 5B, and 6 adjacent the bond pads 42A, 42B and extending from the short side of the base 80 and diaphragm 60. The attachment configuration between the base 80 and the diaphragm 60 may define a discontinuity that allows at least one electrical trace to connect outside said capacitive gap 64 to at least one electrode positioned at least partially within the capacitive gap 64. The vent 66 may also allow the passage of fluid between the housing cavity 25 and the capacitive gap 64.

The underside 62 of the diaphragm 60 may be bonded to the base 80 along a continuous bond line 74 which is the attachment point about the perimeter of the capacitive gap 64. The sensor 40 may be a capacitive pressure sensor, wherein the diaphragm 60 may be designed to flex slightly and change the height of gap 64 when the diaphragm's top surface 68 and bottom surface 62 are exposed to different pressures. The diaphragm 60 and base 80 may be made from the same material or from different materials that are amenable to bonding and whose difference in thermal expansion coefficient may be such that the desired thermal properties may be obtained (either thermal stability or a known response to thermal changes). Materials for the diaphragm 60 and the base 80 may include glass, fused silica, quartz, sapphire, diamond, ceramic, silicon and its derivatives, germanium, SiGe and its derivatives.

Figure 5A:
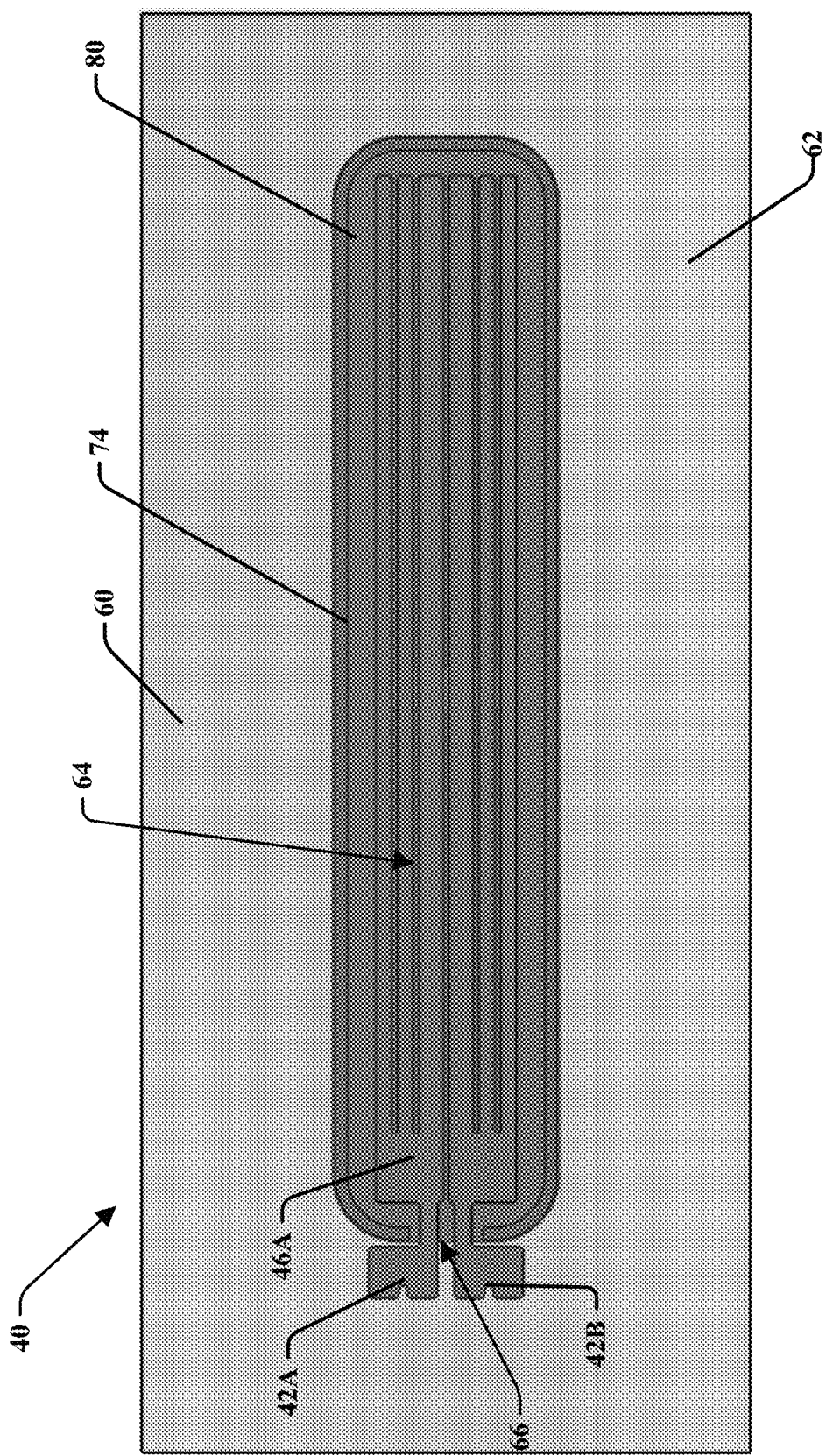
FIG. 5A is a top schematic view of a known sensor component of the implant separate from an implant housing.
Figure 5B:
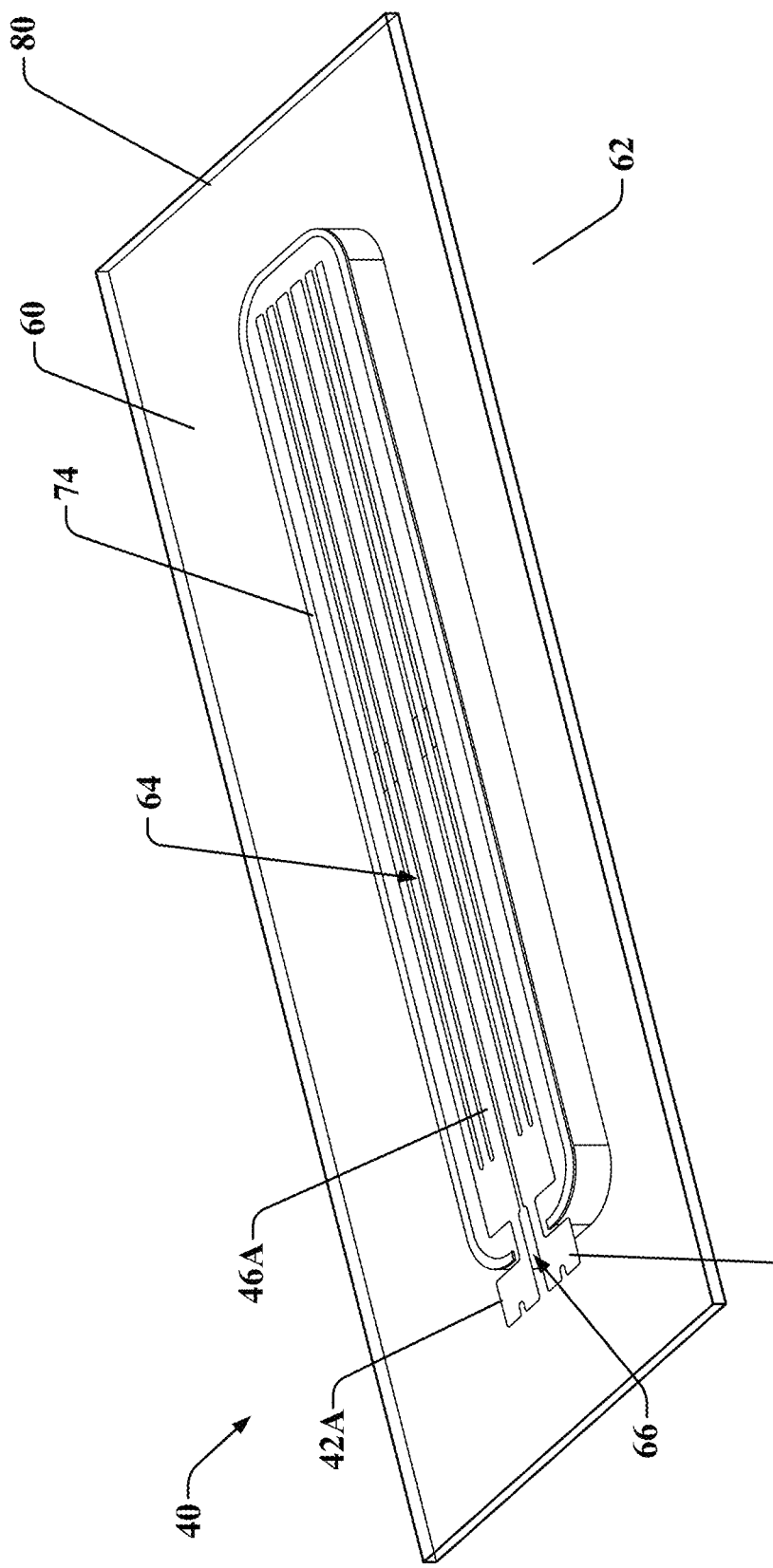
FIG. 5B is a top perspective schematic view of the known sensor component of the instant separate from the implant housing.

FIG. 5A is a top view of the sensor component 40 that illustrates how the bond line 74 surrounds the capacitive gap 64 except for the vent 66. Generally, the bond line 74 completely encircles the perimeter of the gap 64 (as a circle, square, oval, or some other shape). In this embodiment, the sensor 40 includes a parallel plate capacitor with a fixed electrode on the base 80 (which may be made of silicon) and a movable electrode on the diaphragm 60 (which may be made of glass) wherein external pressure on the implant 10 causes the glass diaphragm 60 to deflect, changing the capacitance and thus the implant's output frequency. Equation 1.1 below has been found to reflect this relationship:

$$f = \frac{1}{2\pi\sqrt{LC}} \text{ and } C = \frac{\varepsilon A}{d} \qquad \text{Equation 1.1}$$

Figure 8:
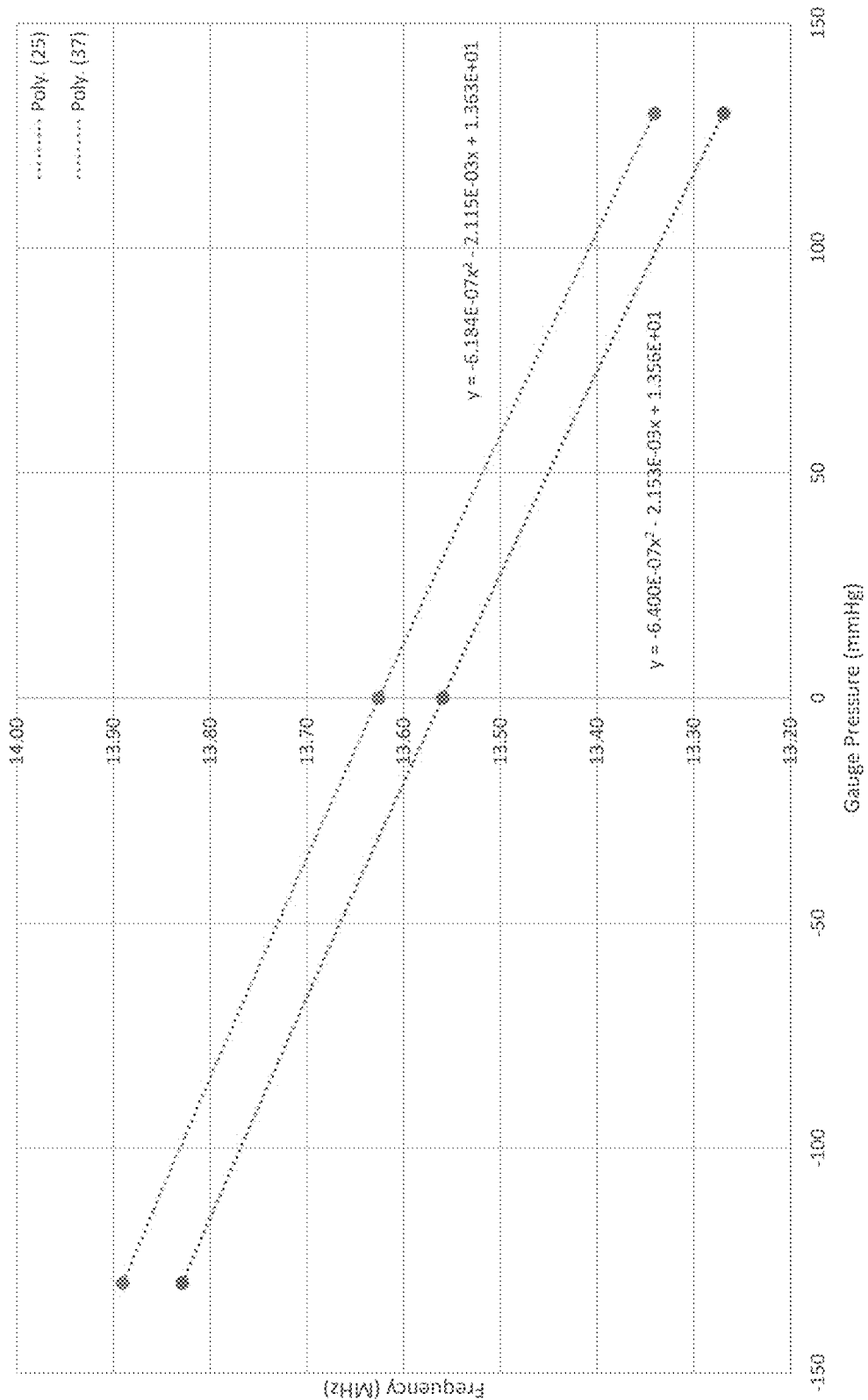
FIG. 8 is a graph that represents frequency v. pressure derived from simulations of known capacitor sensor.

Here, f is the implant's resonant frequency, L is the inductance of an attached inductor 30, C is the capacitance and d is the distance between the capacitor's electrodes 42A and 42B. In some embodiments, the implant 10 has experienced temperature induced offset of frequency between 80-90 kHz. This type of frequency offset has been identified to correspond with smaller capacitance and with larger gaps between the electrodes. FIG. 8 illustrates a graph that represents frequency v. pressure during simulations of the implant 10 of FIGS. 5A and 5B. It illustrates that there exists a 66 kHz frequency difference or error between the implant exposed to an environment of 25C temperature (upper curve) than when exposed to an environment of 37C temperature (lower curve). This translates to a 31.3 mmHg difference that may be due to gas expansion within the cavity 25 as well as different coefficients of thermal expansion between the glass diaphragm 60 and the silicon base 80.

Figure 6:
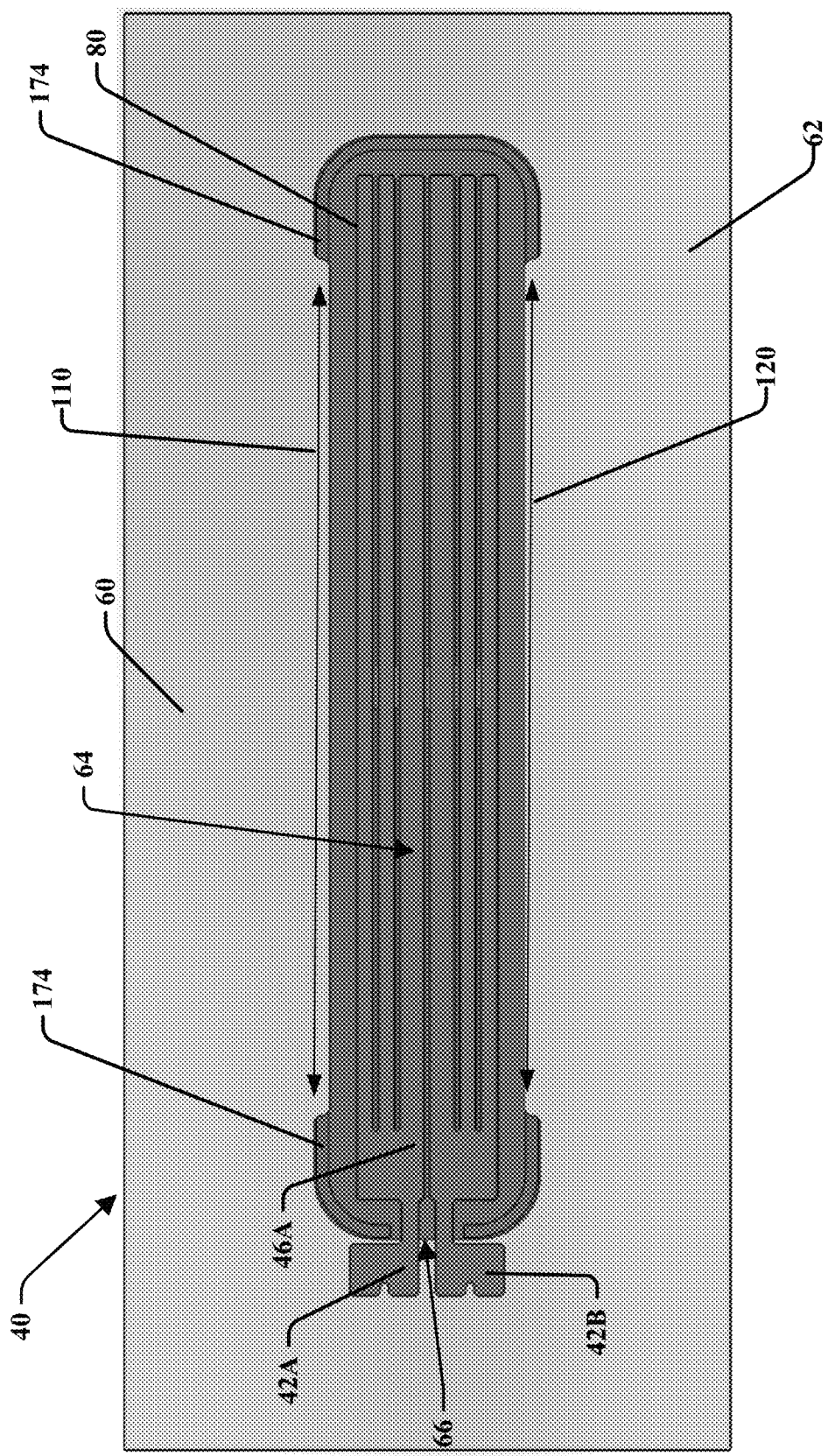
FIG. 6 is a top schematic view of a sensor component of the instant disclosure separate from the implant housing.

FIG. 6 illustrates an alternative embodiment of the implant 10. In this embodiment the sensor 40 is illustrated as a standalone unit as in previous embodiments but in this case the base 80 includes open portions or discontinuities 110, 120 along a discontinuous bond line 174 between the perimeter of the base 80 and the diaphragm 60. These open portions define spaces or discontinuities 110, 120 positioned along the discontinuous bond line 174 to provide a measured opening between the housing cavity 25 and the capacitive gap 64 defined between the base 80 and the diaphragm 60.

This configuration may be useful in either a parallel capacitor arrangement or a series capacitor arrangement. In parallel, one electrode may be positioned on the diaphragm 60 and one electrode on the base 80 and including the capacitive gap 64 therebetween and exposed to the cavity 25 of the housing 20 along discontinuities 110, 120 that extend along a measured portion of the length of the electrodes. The "series capacitor" embodiment includes two electrodes positioned along the diaphragm 60 and one electrode along the base 80. The parallel capacitor embodiment may provide twice the capacitance for the same electrode area and gap height as the serial capacitor embodiment which may provide an advantage in performance and design flexibility. The series capacitor may simplify fabrication of and simplify connection to the sensor 40. Both the series and parallel capacitor arrangements in addition to the discontinuous bond line 174 including discontinuities 110, 120 have been identified to have an effect of increased sensitivity, as well as frequency offset compensation.

The base 80, the diaphragm, or both may be formed to include the discontinuities 110, 120 thereon in an optimized configuration to establish the desired exposure of the capacitive gap 64 to the environment within the cavity 25 in accordance with the findings herein. The particular length and location of the discontinuities 110, 120 have been identified to provide a direct benefit of increasing sensitivity of the sensor 40. Additionally, the discontinuities 110, 120 provide indirect benefits, which allow for design tradeoffs to other features of the implant 10 that would otherwise decrease the sensitivity of the implant 10. For example, the discontinuities 110, 120 allow for the electrodes 46A, 46B to be smaller in order to increase Q value while maintaining a desired level of sensitivity. It is the smaller electrodes that improve Q value and the discontinuities 110, 120 that increase sensitivity. Likewise, the discontinuities 110, 120 may allow for increasing the height of the capacitive gap 64, or to increase diaphragm thickness in an effort to reduce a "pull-in" effect between the electrodes. Further, the discontinuities 110, 120 may be useful in preventing frequency offset that has been caused by exposing the implant 10 to various temperatures, such as between ambient temperature and the temperature within the body of a patient.

The discontinuities 110, 120 may be provided in the base 80 (fixed silicon electrode) to allow the diaphragm 60 (moveable glass electrode) to have a more compliant glass membrane by increasing pressure sensitivity (kHz/mmHg) and also allowing for the increase of the structural thickness of the diaphragm 60 while maintaining pressure sensitivity.

Further, it has been identified that a change in temperature may cause material deflection leading to change in capacitive gap due to (i) gas expansion inside the capacitive gap 64, or (ii) coefficient of thermal expansion (CTE) mismatch between the dissimilar materials (e.g. glass vs. silicon). As the implant is moved from room temperature (25 C) to body temperature (37 C), gas expansion within the implant may cause displacement of the sensor materials, leading to change of capacitive gap 64 height in a different direction than the displacement caused by CTE mismatch between the dissimilar materials. The experienced temperature difference causes bond line strain due to CTE mismatch which may cause the gap to decrease while gas expansion within the capacitive gap 64 may cause the gap height to increase. By introducing the discontinuities 110, 120 with an optimized length between the base 80 and the diaphragm 60, the net capacitance change due to these conflicting effects may be reduced or even canceled.

Figure 7:
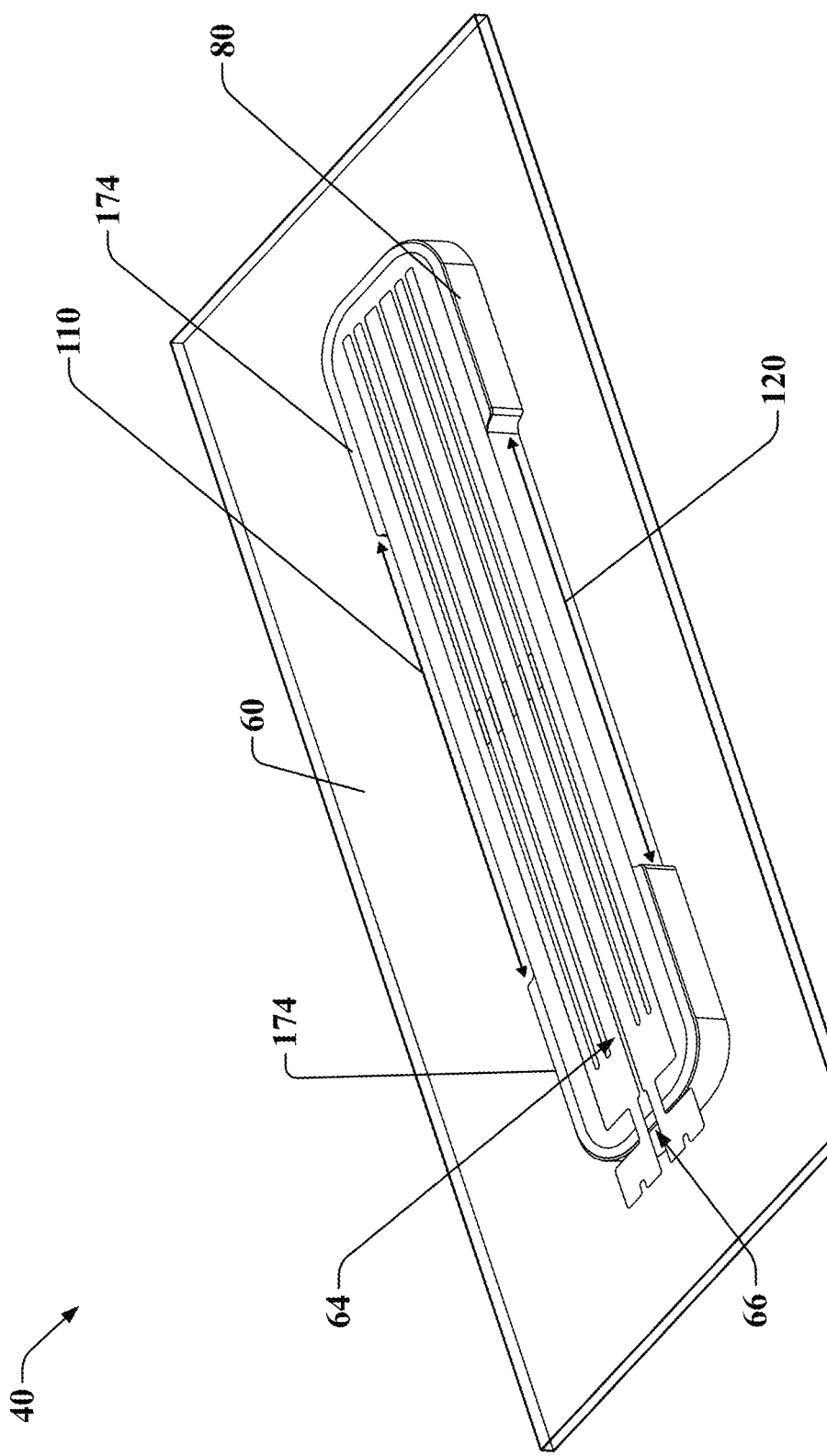
FIG. 7 is a top perspective schematic view of the sensor component of the instant disclosure separate from the implant housing.

Notably, the embodiment of FIGS. 6 and 7 as well as the graphs illustrated by FIGS. 8-15 are directed to merely one embodiment of the implant and are provided by way of an example only as various different implant embodiments are contemplated by this application.

Figure 9:
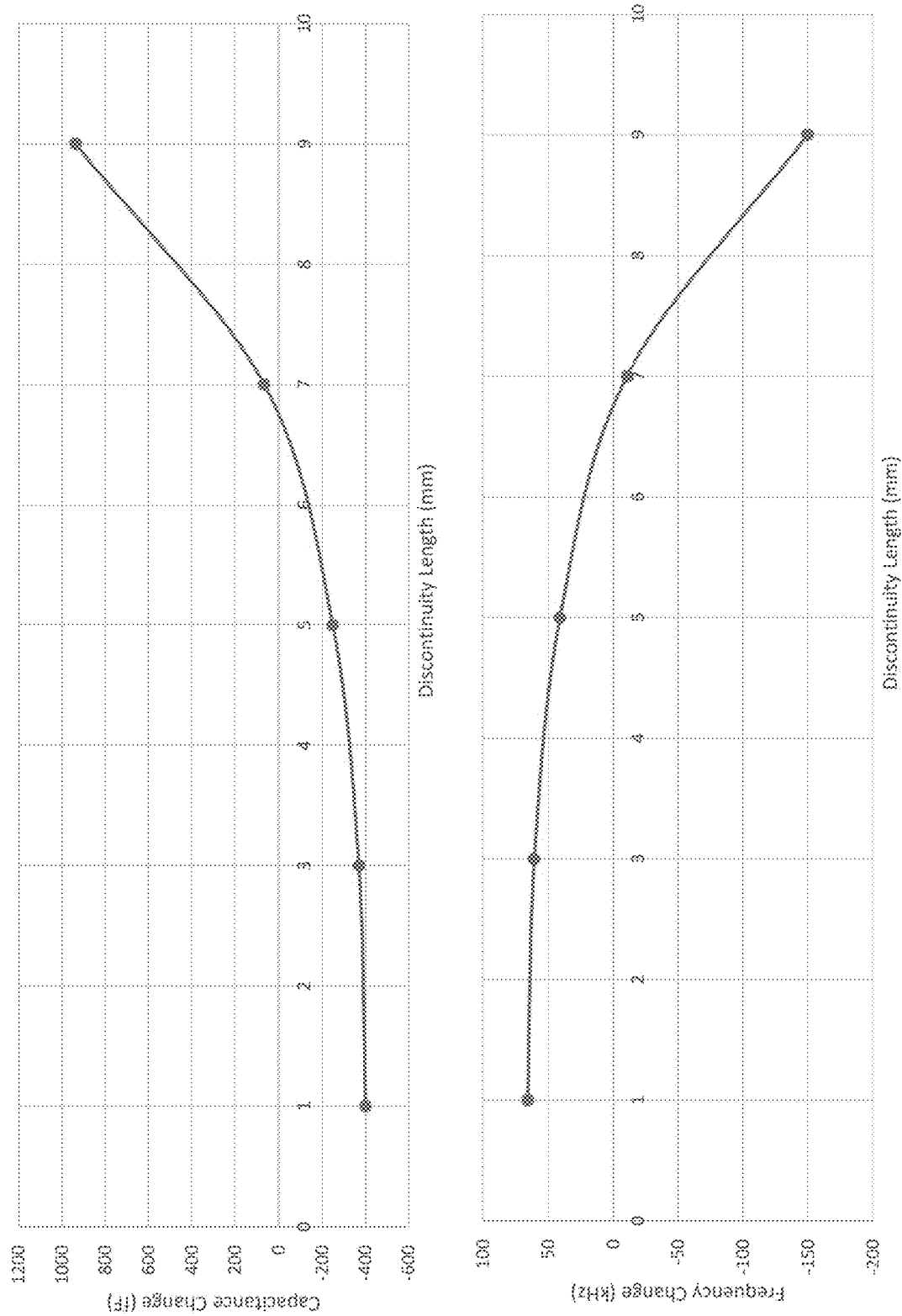
FIG. 9 includes a top graph that represents capacitance v. discontinuity length and a bottom graph that represents frequency v. discontinuity length of the implant of the instant disclosure.

In one embodiment, an optimized length of the discontinuities 110, 120 may be determined by the graphs of FIG. 9. FIG. 9 includes a top graph that represents capacitance change vs. discontinuity length (of discontinuities 110, 120) of the implant 10 of FIG. 6. The top graph illustrates that as the discontinuity length is 1 mm, there is a capacitance change of about −400 fF. However, as the discontinuity length approached 6 or 7 mm, the change in capacitance approaches 0 fF. Further, as the discontinuity length is increased passed 7 mm, the capacitance change (fF) begins to increase to over 800 fF.

The bottom graph of FIG. 9 represents the corresponding frequency change vs. discontinuity length of the implant 10 of FIG. 6. The bottom graph illustrates that as the discontinuity length is 1 mm, there is a frequency change over about 50 kHz. However, as the discontinuity length approached 6 or 7 mm, the frequency change approaches 0 kHz. As the discontinuity length is increased passed 7 mm, the frequency change begins to increase to over −150 kHz. Notably, the top and bottom graphs of FIG. 9 illustrate various simulations performed over a range of temperature changes, observing the capacitance change and the frequency change relative to the discontinuity length.

Figure 10:
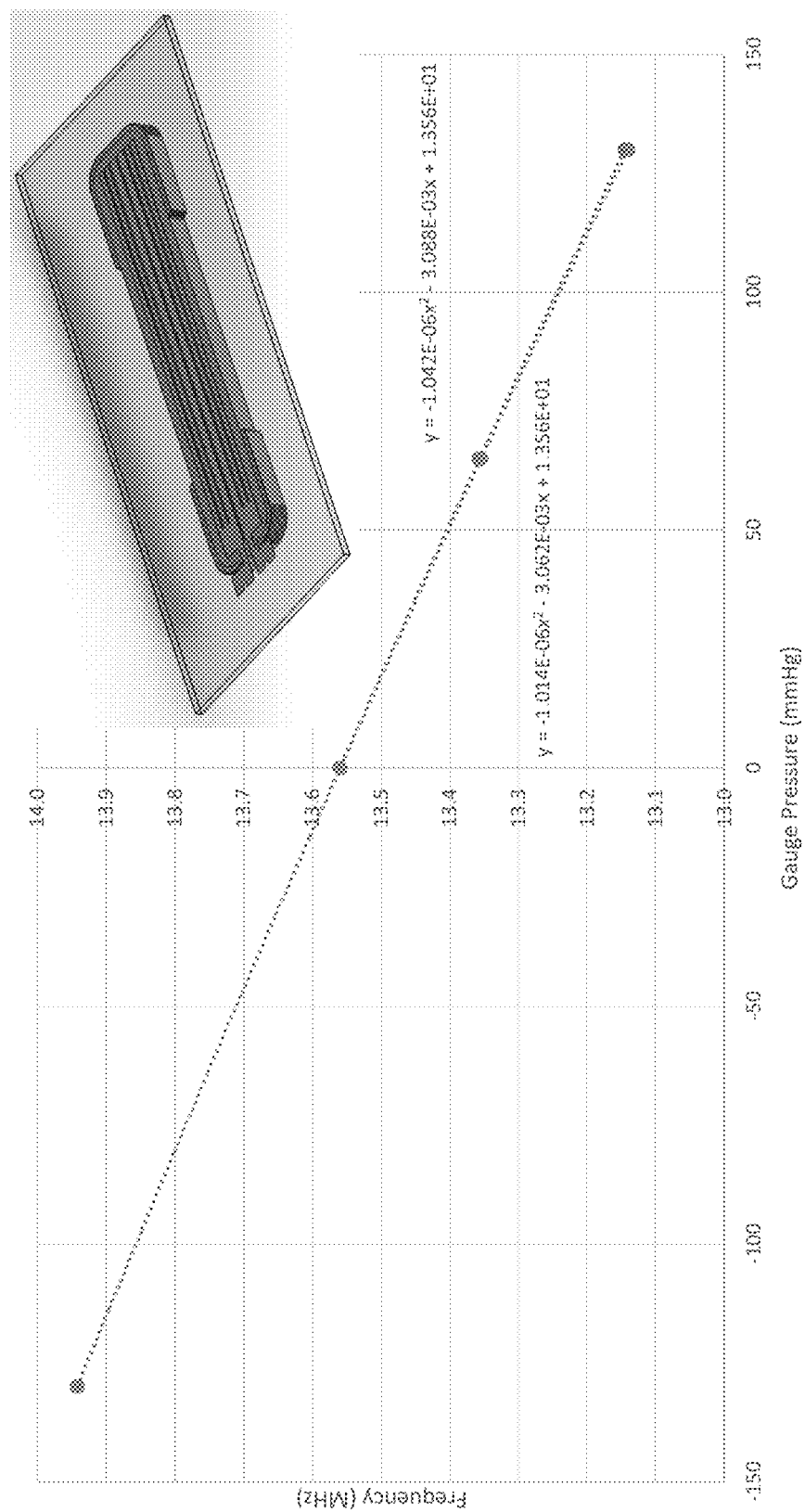
FIG. 10 is a graph that represents frequency v. pressure derived from simulations of an embodiment of the implant of the instant application.

FIG. 10 is a graph that represents frequency v. pressure during simulations of an embodiment of the implant 10 of FIG. 6. FIG. 10 illustrates an optimized embodiment that cancels the different displacements caused by the coefficient of thermal expansion of unrelated materials between the diaphragm 60 and the base 80. As in FIG. 8, there are two curves on the graph, one representing implant performance at 25 C and the other at 37 C. However, the discontinuities 110, 120 in the FIG. 10 graph of the sensor 40 have corrected the temperature offset seen in FIG. 8, and now the two curves are nearly identical. In this embodiment, the diaphragm 60 is made from a glass material that includes a thickness of about 195 um and wherein the discontinuities 110, 120 are designed along the bond line 174 and include a length along the sides of the base 80 that are about 6.75 mm. This optimized sensor 40 embodiment was found to have a capacitive change of about 9 fF and a frequency change of about −1.5 kHz when this sensor 40 was exposed to an environment of 25 C and then to an environment of 37 C. This configuration translates to a gauge pressure of 0.5 mmHg. This optimized sensor 40 accounts for gas expansion within the cavity 25 and thermal coefficient difference between the glass diaphragm 60 and the silicon base 80.

Figure 11:
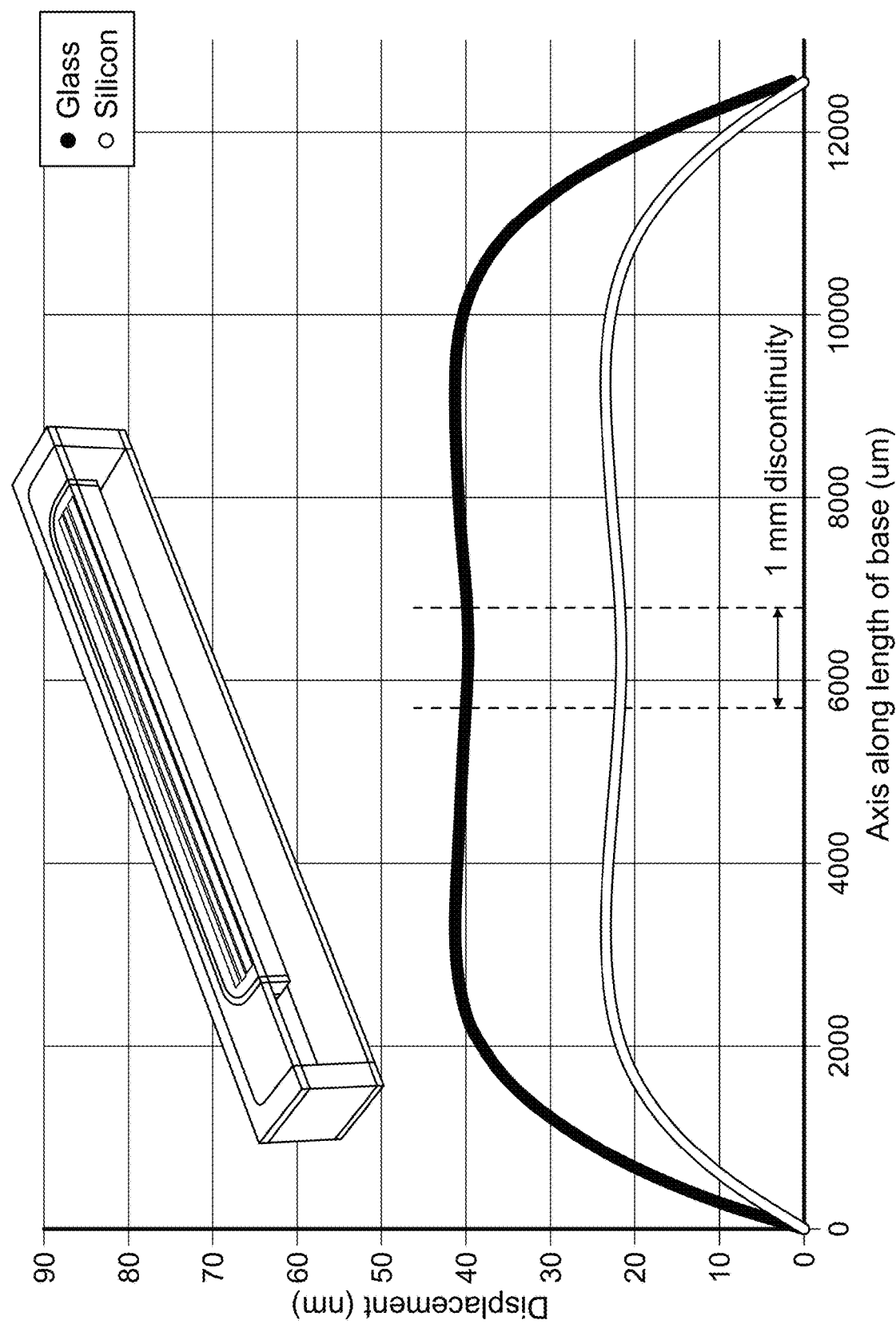
FIG. 11 is a graph that represents change in diaphragm displacement due to temperature v. axis length derived from simulations of embodiments of the implant of the instant application.
Figure 12:
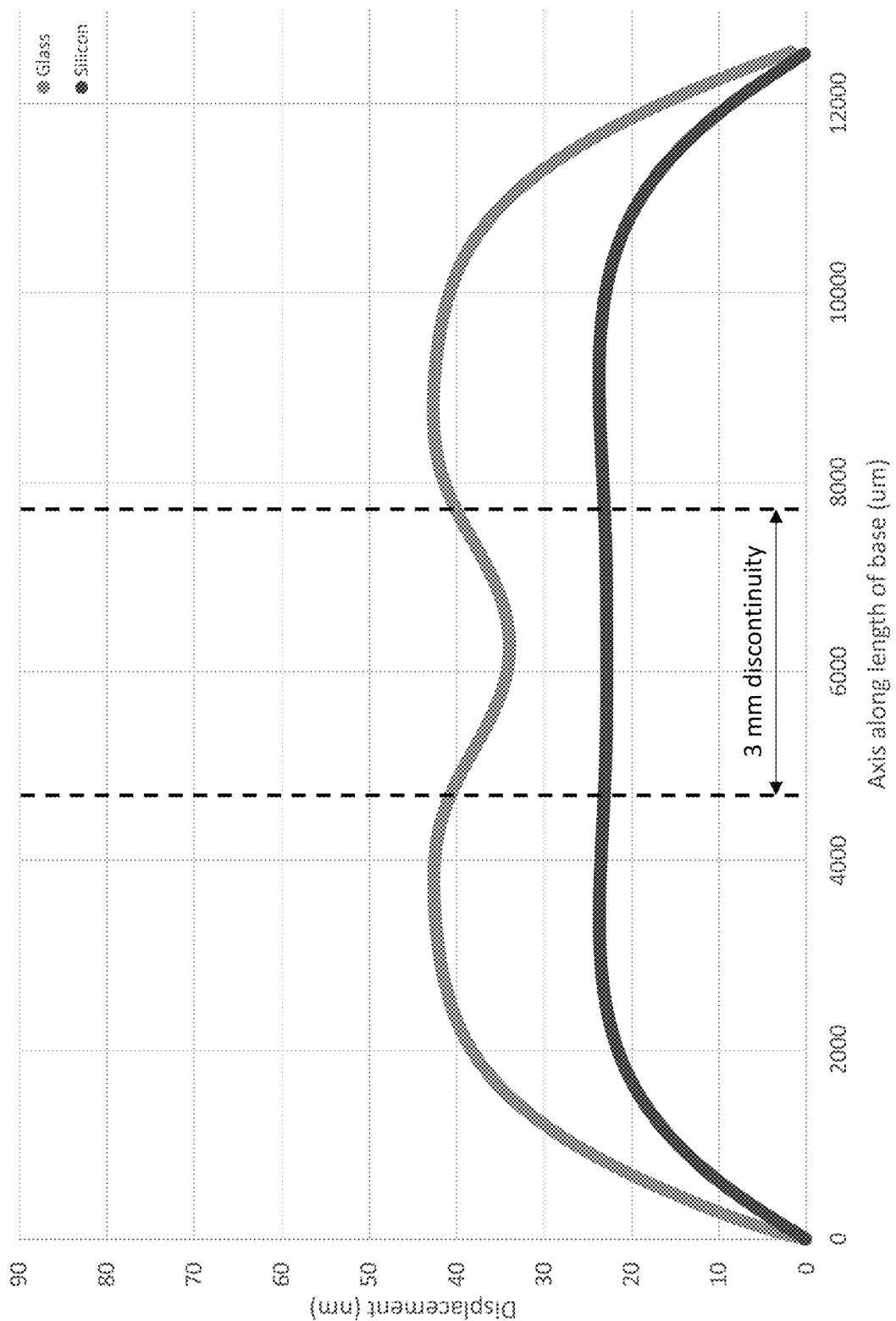
FIG. 12 is a graph that represents change in diaphragm displacement due to temperature v. axis length derived from simulations of embodiments of the implant of the instant application.
Figure 13:
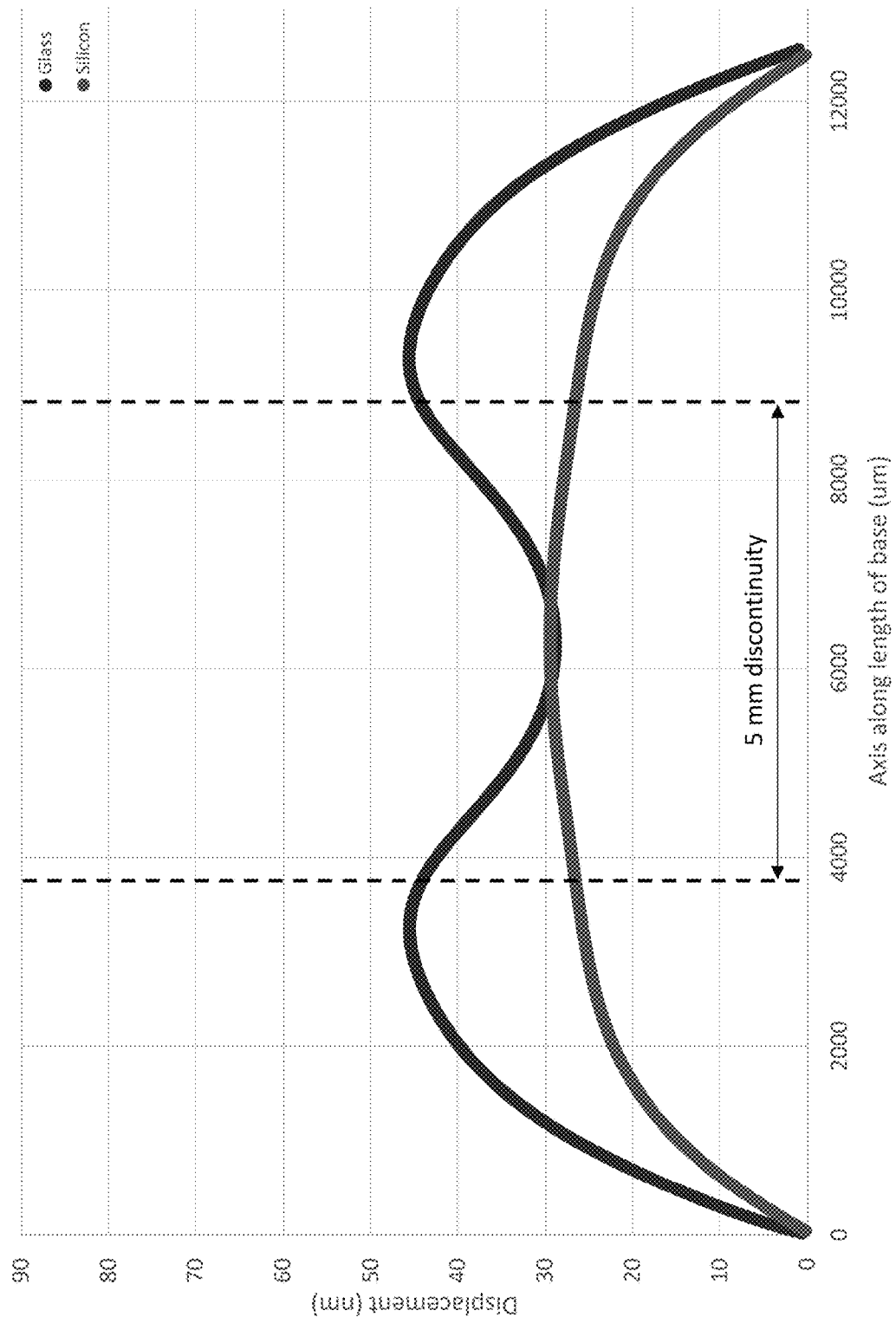
FIG. 13 is a graph that represents change in diaphragm displacement due to temperature v. axis length derived from simulations of embodiments of the implant of the instant application.
Figure 14:
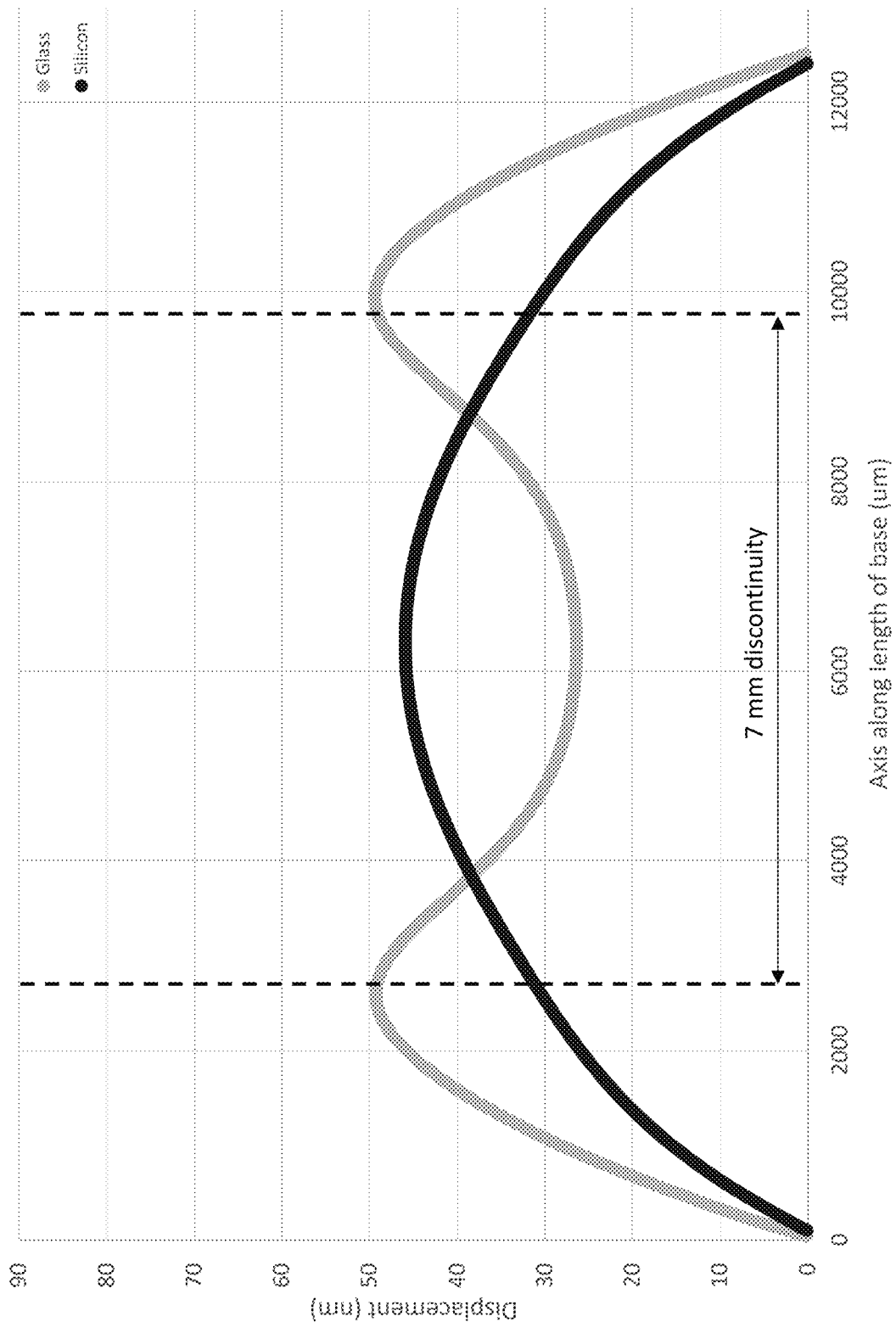
FIG. 14 is a graph that represents change in diaphragm displacement due to temperature v. axis length derived from simulations of embodiments of the implant of the instant application.
Figure 15:
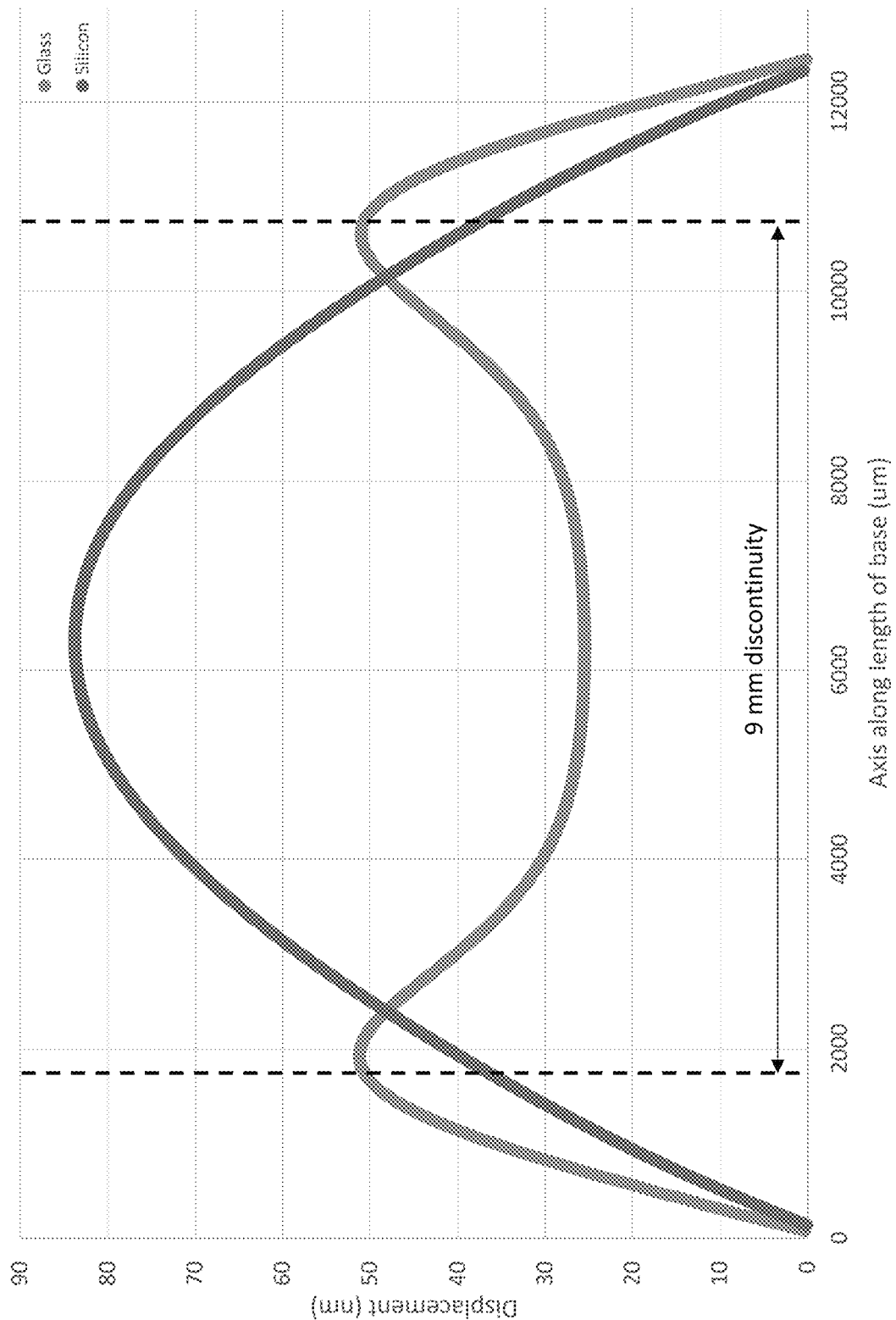
FIG. 15 is a graph that represents change in diaphragm displacement due to temperature v. axis length derived from simulations of embodiments of the implant of the instant application.

FIGS. 11 through 15 each include a graph that represents displacement vs. axis length during simulations of different embodiments of the implant 10 of FIG. 6 wherein the discontinuities 110, 120 have a different length. FIGS. 11-15 illustrate the vertical displacement (nm) and location of displacement along the axis of the sensor 40 of the glass diaphragm 60 relative to the silicon base 80 of FIG. 6. In each of FIGS. 11-15, the line labeled "glass" illustrates the difference in displacement (nm), at constant pressure, of the glass diaphragm 60 that occurs between 25 C and 37 C ambient temperature. The line labeled "silicon" illustrates displacement difference between 25 C and 37 C of the silicon base 80. FIG. 11 includes a discontinuity length of 1 mm, FIG. 12 includes a discontinuity length of 3 mm, FIG. 13 includes a discontinuity length of 5 mm, FIG. 14 includes a discontinuity length of 7 mm, and FIG. 15 includes a discontinuity length of 9 mm. Considered together, FIGS. 11-15 illustrate the wide range of parametric variation that can be achieved by simply adjusting the lengths of the discontinuities 110, 120. Further, it was discovered that it may be possible to cancel out the displacement caused by both CTE difference experienced between dissimilar materials and the displacement caused by gas expansion as the implant is exposed to different temperatures (i.e. from room to body temperature). Here the glass diaphragm has a different coefficient of thermal expansion than the silicon base wherein FIG. 14 illustrates an embodiment wherein the discontinuity length of about 7 mm assists to reduce the material displacement experienced by the dissimilar materials due to their different CTEs. In FIG. 14, the area under each curve is approximately equal, indicating the point at which the two temperature effects on capacitance are in balance. Each respective curve identifies measurements taken from the bottom surface of the glass diaphragm and a top surface of the silicon base.

All of the variations and embodiments discussed herein will accrue the benefits discussed herein from careful design of the bond line discontinuities 110, 120 of FIG. 6. In addition to the benefits already discussed, it should be appreciated that any reduction in the length of the perimeter bond line 174 will also reduce the effects of stress caused by bonding, including sensor inaccuracy due to long term relaxation of stress, risk of cracking, delamination and other stress related effects.

The same benefits may accrue from other lengths, locations, and numbers of discontinuities besides those depicted in FIG. 6. Discontinuities may occur on the short sides instead of, or in addition to the long sides of bond line 174, as well as at one or more corners of the perimeter. Discontinuities may be asymmetrical with respect to one another. For certain embodiments, a number of smaller discontinuities, for example a dotted-line pattern, may provide benefit. Other embodiments may benefit from retention of a length of bondline at the midpoint of the long side of the capacitive gap 64 of FIG. 6, possibly intended to limit gap change near the center of the diaphragm, typically the region of largest deflection. Finally, there may be benefit in placing discontinuities that are partial; that is, their width is thinner than that of the retained portion of the perimeter bondline 174, so their stress profile is lower, but they do not vent the capacitive gap 64.

It is further observed that in a MEMS fabrication process, varying device performance parameters with a simple change, such as the discontinuity length, location, shape, and number, provides a benefit. Such a change may require a minimal number of mask changes, perhaps only a single mask, depending on the specific fabrication process used.

It is further observed that the retained portion of the bond line 174 may be made wider, to strengthen the bond between diaphragm 60 and base 80. This may offset any weakening of the bond caused by introduction of the discontinuities 110, 120.

Figure 16:
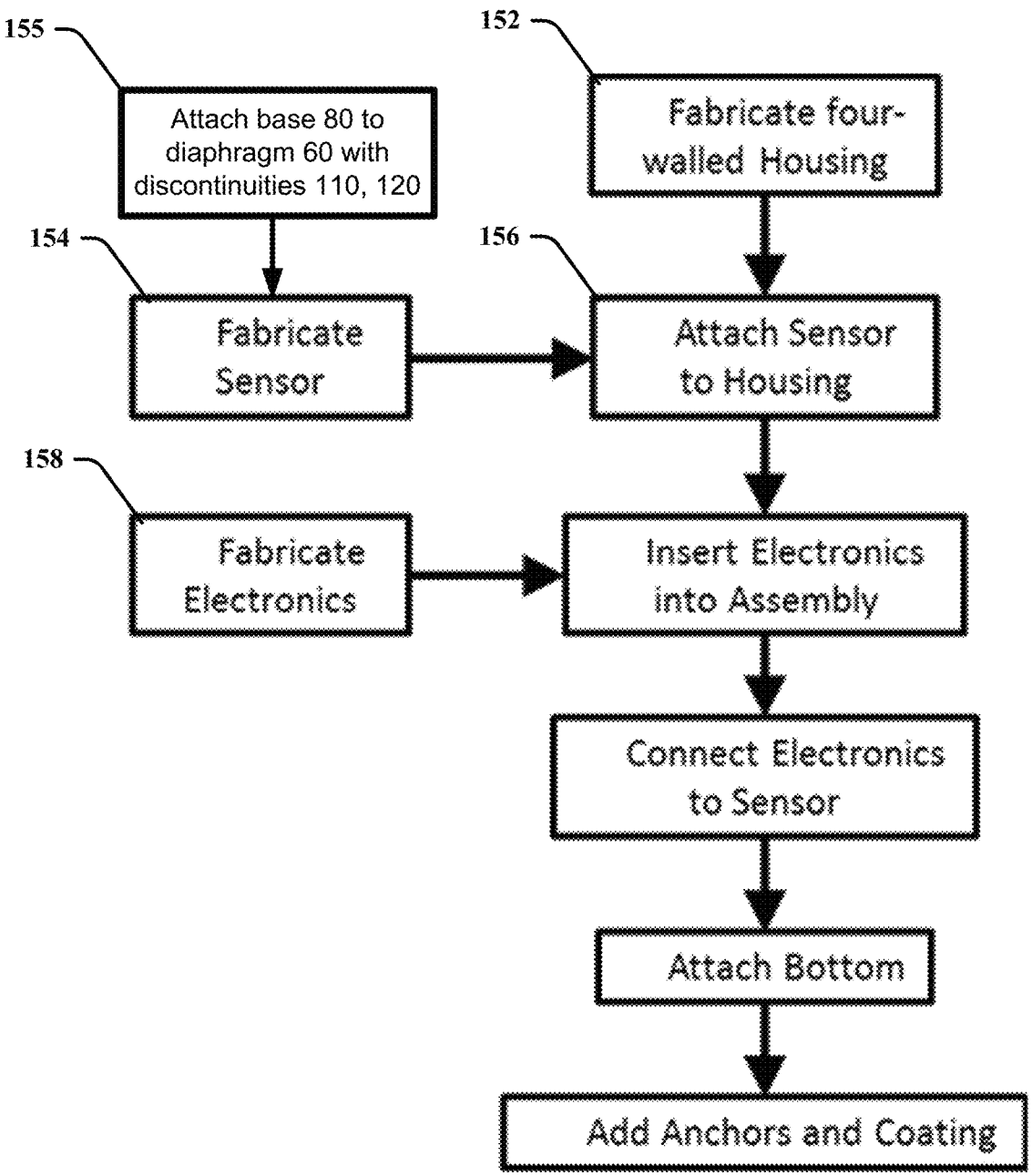
FIG. 16 is a flowchart illustrating a method of assembling an implant in accordance with the present disclosure.

FIG. 16 is a flowchart that illustrates an exemplary method for assembling the implant 10. FIG. 16 represents one possible process for a typical embodiment of the implant 10. Some steps may not be necessary, or can be carried out in a different sequence, or may include other steps.

In step 152, an implant housing may be formed having four sides 52, 54, 56, and 58. However, this disclosure is not limited as other shaped housings 20 are contemplated, such as cylindrical, triangular, pentagonal, hexagonal, or any shape, including asymmetrical configurations. The sensor 40 may be fabricated as a standalone device, described by step 154. In one embodiment, a silicon wafer (base) is provided wherein a portion is etched away to partially form a cavity. An electrode may be applied to a surface of the silicon wafer within the partially formed cavity. The electrode may be formed by metal deposition and also include dielectric deposition. A glass wafer (diaphragm) may be provided that also includes an electrode thereon. The electrode may be formed by metal deposition. Here, in step 155, the silicon wafer base 80 may be formed to include discontinuities 110, 120 thereon in accordance with the findings herein. The shape and length of the implant 10 may assist in optimizing the length and location of the discontinuities 110, 120. The optimized length and location of the discontinuities 110, 120, such as determined by the graphs of FIG. 9, have been identified to be useful in preventing frequency offset that has been caused by exposing an embodiment of the implant 10 to various temperatures, such as between ambient temperature and the temperature within the body of a patient. The glass wafer may be bonded to the silicon wafer along the bond line thereby forming the cavity and the capacitive gap with the aligned electrodes at least partially therein. Further etching, thinning, grinding, polishing, or dicing may occur to remove material from either the glass or silicon wafer to form the sensor 40.

Figure 3:
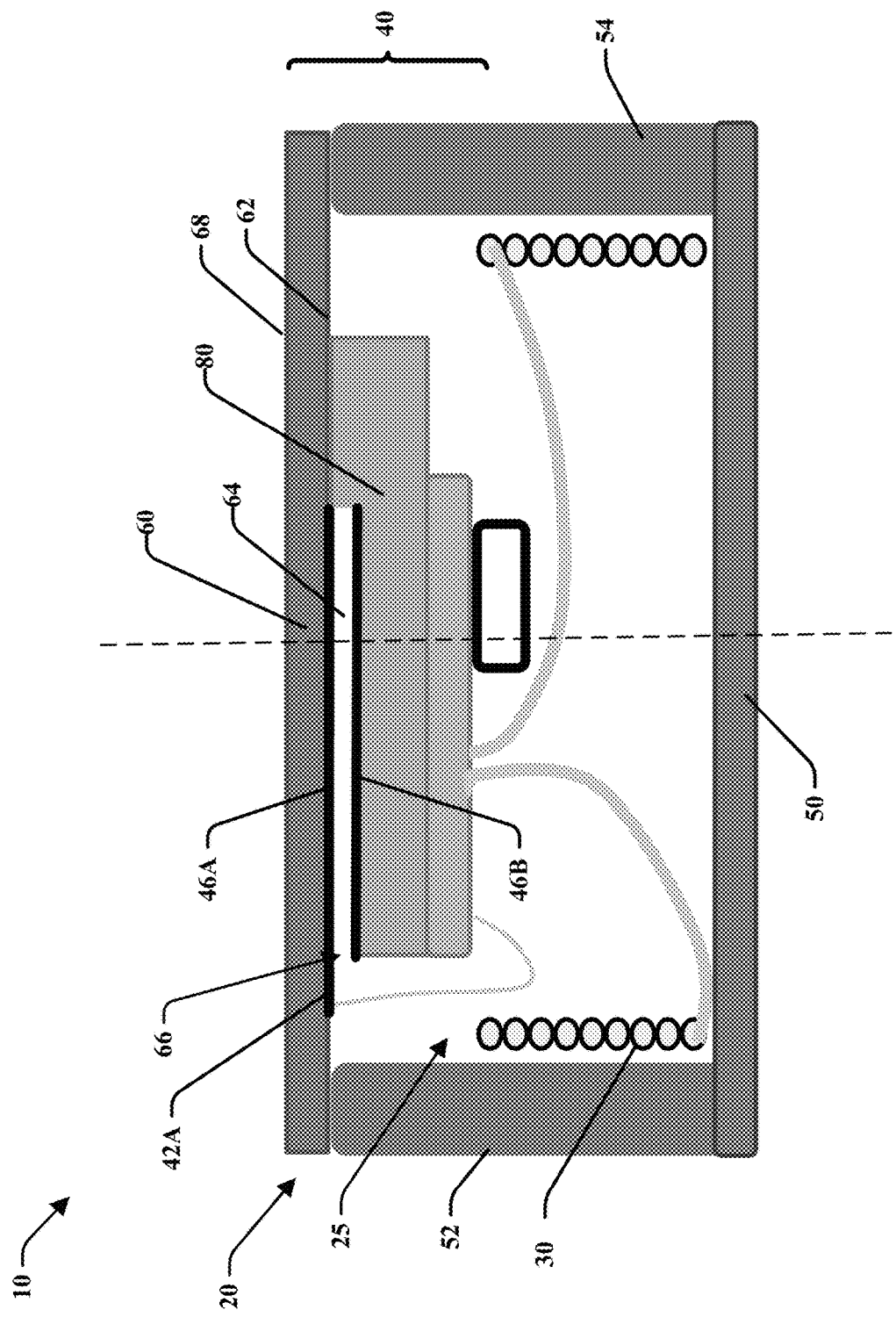
FIG. 3 is a schematic cross-sectional view of the implant of FIG. 1.
Figure 4:
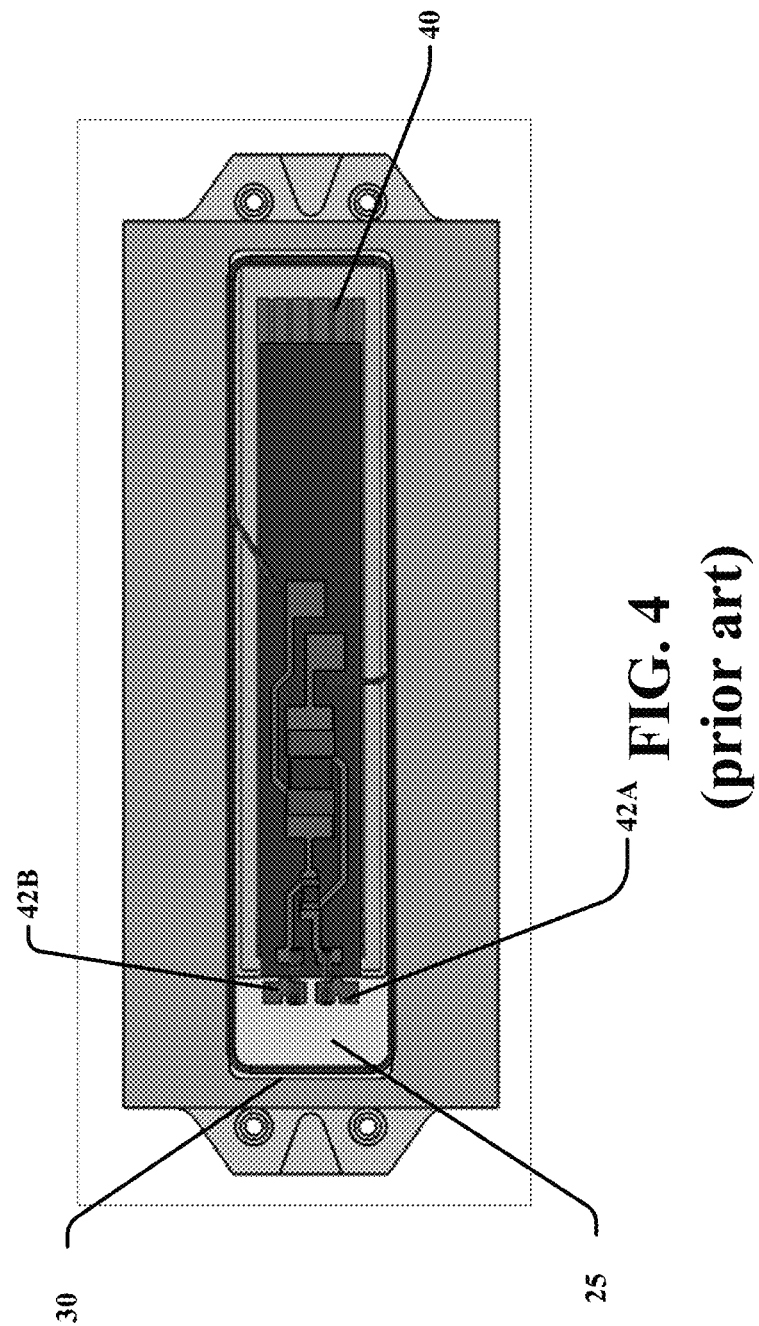
FIG. 4 is a bottom schematic view of a portion of a partially assembled implant with a printed circuit board for an embodiment of the implant.

The sensor 40 may be attached to the housing 20 per step 156. FIGS. 3 and 4 illustrate the sensor 40 attached to the sidewalls 52 and 54 of the housing 20, such that the floating base 80 resides inside the cavity 25. The diaphragm 60 may have a perimeter that overlaps the base 80 sufficiently to attach to the top surfaces of the side walls by one of the hermetic attachment methods available.

The assembly or fabrication of electronics may occur in step 158. The implant 10 includes an antenna coil 30 that may be placed into the cavity 25 of the housing 20. Other electronic components, which may include one or more pressure sensors, may also be placed inside housing 20. The electronic components may be placed at least partially inside the region defined by the coil 30, or outside of this region. The electronic components may be positioned and attached along the inner surface 62 of the diaphragm 60. The coil 30 may be positioned such that it surrounds the floating base 80 and the electronic components partially or fully. The electronics and coil 30 may be assembled and interconnected electrically prior to insertion into the housing 20, or portions of the electronics and coil 30 may be inserted and then interconnected. By positioning the base 80 within the cavity 25 in a floating arrangement relative to the position of the coil 30, it may reduce the overall size of the implant 10. Additionally, during assembly, this configuration allows for accessibility to the electrodes without through vias or holes.

In the case where implant 10 contains a pressure sensor 40, the internal electronic components may include one or more pressure sensors such as MEMS pressure sensor components and the top wall 60 may be a diaphragm such as a flexible membrane. The top wall 60 and electrodes 46A, 46B may communicate pressure by slight vibrations. Also, a gas, a fluid, vacuum, desiccant material, getter material, or a gel may fill the cavity 25 formed by the housing 20. In another embodiment, the bottom wall 50 may also be a diaphragm such as a flexible membrane which may include additional electrical components that may also be part of a sensing electronic circuit (not shown). In either embodiment, pressure measurements may be transduced directly into an electronic signal of a sensing circuit or component.

The embodiments disclosed herein may benefit from having the final sidewalls attached in a vacuum environment or a known pressure. The cavity of the housing of the implant may be a sealed vacuum encapsulation. Additionally, the cavity of the housing may be sealed having a known pressure. This may assist to prevent internal pressures inside the housing from varying with temperature. Alternatively, the internal volume may be filled with an inert gas to limit corrosion of the internals. This may reduce the risk of problems related to moisture or other particulates.

In one embodiment, the implant sensor transmits a signal in response to an excitation pulse at a desired frequency range. In one embodiment, that frequency range is between 5 MHz to 30 MHz, and more particularly between 10 MHz to 20 MHz, or between 12 MHz to 15 MHz, and preferably between 13 MHz to 14 MHz.

While the apparatus and method of subject invention have been shown and described with reference to preferred embodiments, those skilled in the art will readily appreciate that changes and/or modifications may be made thereto without departing from the spirit and scope of the subject invention.

Having thus described the invention, we claim:

1. An implant comprising:
 a housing that defines a housing cavity;
 a sensor connected to said housing comprising:
  a diaphragm configured to flex in response to external changes in pressure;
  a floating base attached to said diaphragm to define a capacitive gap between said diaphragm and said floating base, said attachment being positioned along a perimeter of said capacitive gap, wherein said capacitive gap includes at least one patterned electrode positioned on said floating base;
  wherein said floating base is positioned entirely within said cavity; and
  wherein said attachment along said perimeter contains at least one open portion.

2. The implant of claim 1, wherein said floating base is attached only to said diaphragm.

3. The implant of claim 1, wherein said sensor is a capacitive pressure sensor.

4. The implant of claim 1, wherein said diaphragm is connected to said housing to form a hermetic seal about said housing cavity.

5. The implant of claim 1, wherein said sensor includes electrical contacts positioned on said diaphragm.

6. The implant of claim 1, wherein said at least one open portion vents said capacitive gap to said housing cavity such that liquid or gas passes between said capacitive gap and said housing cavity.

7. The implant of claim 1, wherein said at least one open portion allows at least one electrical trace to connect at least one electrical contact outside of said capacitive gap to at least one electrode positioned at least partially within said capacitive gap.

8. The implant of claim 1, wherein said capacitive gap includes at least one electrode positioned on said diaphragm.

9. The implant of claim 1, further comprising a coil in electrical communication with said sensor, said coil positioned within said housing.

10. The implant of claim 1, wherein said diaphragm is made of a glass material and said floating base is made of silicon.

11. The implant of claim 10, wherein said diaphragm includes a thickness of about 195 μm and said at least one open portion includes a length of about 6.75 mm.

12. The implant of claim 1, wherein location and size of said at least one open portion are configured to enhance at least one performance parameter of said implant.

13. The implant of claim 12, wherein said at least one performance parameter is selected from the following list: sensitivity to pressure, sensitivity to temperature, mechanical strength, reduction of mechanical stress in said diaphragm, and long-term accuracy.

14. The implant of claim 13, wherein said sensitivity to temperature is achieved by positioning said at least one open portion such that a coefficient of thermal expansion mismatch effect counteracts a gas expansion effect to reduce capacitive gap change due to temperature.

15. An implant comprising:
   a housing that defines a cavity;
   a sensor connected to said housing comprising:
      a diaphragm having at least one diaphragm electrode; and
      a base attached to said diaphragm and positioned entirely within the cavity of said housing, said base including at least one base electrode wherein said base and diaphragm define a capacitive gap between the at least one diaphragm electrode and the at least one base electrode; and
   wherein said base attaches to said diaphragm along a perimeter of said capacitive gap, said attachment including at least one open portion configured to enhance at least one performance parameter of said implant.

16. The implant of claim 15, wherein said base further includes at least one through hole to provide access to electrically connect said at least one base electrode to a component outside said capacitive gap.

17. The implant of claim 15, wherein said diaphragm includes a thickness between about 100 μm to about 300 μm.

18. The implant of claim 15, wherein said implant includes a circuit having a resonant frequency that changes in response to a sensed parameter.

19. The implant of claim 15, wherein said implant is filled with a liquid or gel.

20. The implant of claim 15, wherein said base includes at least one through substrate via (TSV) to electrically connect the at least one of the base electrode and said diaphragm electrode to a component outside said capacitive gap.

21. The implant of claim 15, wherein said diaphragm includes a thick region and a thin region wherein said thin region is aligned with said capacitive gap.

22. The implant of claim 15, wherein said at least one performance parameter is selected from the following list: sensitivity to pressure, sensitivity to temperature, mechanical strength, and long term accuracy.

23. The implant of claim 22, wherein said sensitivity to temperature is achieved by positioning said at least one open portion such that a coefficient of thermal expansion mismatch effect counteracts a gas expansion effect to reduce capacitive gap change due to temperature.

24. The implant of claim 15, wherein said cavity of the housing of the implant is filled with vacuum, inert gas, other gas species, or gas at a predetermined pressure.

25. The implant of claim 15, wherein said cavity of the housing of the implant includes a getter material.

26. An implant comprising:
   a housing having a plurality of walls and at least one opening;
   a sensor connected to an opening of said at least one opening in said housing, said sensor comprising:
      a first layer having a first dimension;
      a second layer having a second dimension shorter than said first dimension;
      wherein said second layer is positioned entirely within said housing and a surface of said first layer is exposed to the exterior of said housing;
      wherein said second layer is attached to said first layer to define a capacitive gap between layers, said attachment being positioned along a perimeter of said capacitive gap, wherein said capacitive gap includes at least one patterned electrode positioned on said second layer;
      wherein said attachment along said perimeter contains at least one open portion; and
      wherein a location of said at least one open portion is configured to enhance at least one performance parameter of said implant.

* * * * *